United States Patent
Bill et al.

(10) Patent No.: US 7,507,574 B2
(45) Date of Patent: Mar. 24, 2009

(54) RECOMBINANT SACCHAROMYCES CEREVISIAE EXPRESSING CHIMERIC GLUCOSE TRANSPORTERS

(75) Inventors: Roslyn Bill, Knowle (GB); Eckhard Boles, Dreieich (DE); Lena Gustafsson, Mölndal (SE); Stefan Hohmann, Lerum (SE); Christer Larsson, Mölndal (SE); Karin Elbing, Göteborg (SE)

(73) Assignee: Gothia Yeast Solutions AB, Kungsbacka (SE)

( * ) Notice: Subject to any disclaimer, the term of this patent is extended or adjusted under 35 U.S.C. 154(b) by 741 days.

(21) Appl. No.: 10/312,783

(22) PCT Filed: Jun. 29, 2001

(86) PCT No.: PCT/GB01/03079

§ 371 (c)(1),
(2), (4) Date: Jul. 21, 2003

(87) PCT Pub. No.: WO02/00880

PCT Pub. Date: Jan. 3, 2002

(65) Prior Publication Data

US 2004/0058429 A1    Mar. 25, 2004

(30) Foreign Application Priority Data

Jun. 29, 2000 (SE) .................................... 0002460
Nov. 17, 2000 (SE) .................................... 0004241

(51) Int. Cl.
| | |
|---|---|
| C12N 1/19 | (2006.01) |
| C12N 15/63 | (2006.01) |
| C12N 15/81 | (2006.01) |
| C12P 21/02 | (2006.01) |
| C12P 1/02 | (2006.01) |
| C07H 21/04 | (2006.01) |
| C07K 14/395 | (2006.01) |
| A23J 1/18 | (2006.01) |
| A23J 1/28 | (2006.01) |
| C12C 11/00 | (2006.01) |

(52) U.S. Cl. .............................. 435/254.21; 435/320.1; 435/69.1; 435/69.7; 435/171; 435/483; 536/23.4; 536/23.74; 530/350; 530/371; 426/16; 426/60

(58) Field of Classification Search ...................... None
See application file for complete search history.

(56) References Cited

U.S. PATENT DOCUMENTS 6,190,883 B1    2/2001 Srivastava et al.

FOREIGN PATENT DOCUMENTS

| EP | 0785275 A2 | 7/1997 |
|---|---|---|
| WO | WO 00/14258 A1 | 3/2000 |

OTHER PUBLICATIONS

Blom et al. May 2000. Applied and Environmental Microbiology. 66(5): 1970-1973.*

(Continued)

*Primary Examiner*—Gary B Nickol
*Assistant Examiner*—Zachary C Howard
(74) *Attorney, Agent, or Firm*—Rothwell, Figg, Ernst & Manbeck

(57) ABSTRACT

The present invention provides a modified *Saccharomyces* yeast which produces significantly lower levels of ethanol than wild-type yeast under aerobic conditions and saccharide concentrations of 2% glucose, and which exhibits a growth rate of at least 30% of the wild-type yeast, preferably containing a chimeric construct of at least 2 saccharide transporters, nucleic acid molecules encoding the chimeras and polypeptides encoded by such sequences, and methods of using the modified yeast for preparing products in the yeast.

23 Claims, 4 Drawing Sheets

Blázquez, Miguel A, et al., "Trehalose-6-phosphate, a new regulator of yeast glycolysis that inhibits hexokinases," *FEBS Letters*, 1993, pp. 51-54, vol. 329. Elsevier Science Publishers.

Bisson, Linda F., "Involvement of kinases in glucose and fructose uptake by *Saccharomyces cerevisiae*," *Proc. Natl. Acad. Sci. USA*, Mar. 1983, pp. 1730-1734, vol. 80.

Bisson, Linda F., "Yeast Sugar Transporters," *Critical Reviews in Biochemistry and Molecular Biology*, 1993, pp. 259-308, vol. 28, No. 4. CRC Press, Inc.

Blomberg, Anders et al., "Microcalorimetric Monitoring of Growth of *Saccharomyces cerevisiae*: Osmotolerance in Relation to Physiological State," *Journal of Bacteriology*, Oct. 1988, pp. 4562-4568, vol. 170, No. 10. American Society for Microbiology.

Boles, Eckhard, et al., "Cloning of a second gene encoding 6-phosphofructo-2-kinase in yeast, and characterization of mutant strains without fructose-2,6-bisphosphate," *Molecular Microbiology*, 1996, pp. 65-76, vol. 20., No. 1.

Bonini, Beatriz M, et al., "Expression of *Escherichia coli otsA* in a *Saccharomyces cerevisiae tps1* mutant restores trehalose 6-phosphate levels and partly restores growth and fermentation with glucose and control of glucose influx into glycolysis," *Biochem J.*, 2000, pp. 261-268, vol. 350.

Brown, Celeste J., et al., "Multiple Duplications of Yeast Hexose Transport Genes in Response to Selection in a Glucose-Limited Environment," *Mol. Biol. Evol.*, Aug. 1998, pp. 931-942, vol. 15, No. 8.

Campbell-Burk, S.L., "High-Resolution NMR Studies of *Saccharomyces cerevisiae*," *Ann. Rev. Microbiol.*, 1987, pp. 595-616, vol. 41.

Davies, Siân, et al., Effects of Overexpression of Phosphofructokinase on Glycolysis in the Yeast *Saccharomyces cerevisiae, Biochemistry*, 1992, pp. 4729-4735, vol. 31.

Diderich, Jasper A., et al., Glucose Uptake Kinetics and Transcription of *HXT* Genes in Chemostat Cultures of *Saccharomyces cerevisiae, The Journal of Biological Chemistry*, May 28, 1999, pp. 15350-15359, vol. 274, No. 22. The American Society for Biochemistry and Molecular Biology, Inc.

Diderich, Jasper et al., "Physiological Properties of *Saccharomyces cerevisiae* from Which Hexokinase II Has Been Deleted," *Applied and Environmental Microbiology*, Apr. 2001, pp. 1587-1593, vol. 67, No. 4. American Society for Microbiology.

Fraenkel, Dan G., "The molecular biology of the yeast *Saccharomyces cerevisiae*: Metabolism and gene expression," in *Carbohydrate Metabolism*, 1982, pp. 1-37, Cold Spring Harbor, N.Y.

Gancedo, Carlos, et al., "Energy-Yielding Metabolism," in *The Yeasts*, Rose and Harrison (Eds.), 1989, pp. 205-259, Second ed. vol. 3. Academic Press.

Gancedo, Juana, "Carbon catabolite repression in yeast," *Eur. J. Biochem.*, 1992, pp. 297-313, vol. 206.

Gancedo, Juana, "Yeast Carbon Catabolite Repression," *Microbiology and Molecular Biology Reviews*, Jun. 1998, pp. 334-361, vol. 62, No. 2. American Society for Microbiology.

Gonzalez, M. Isabel, et al., "Molecular Cloning of *CIF1*, a Yeast Gene Necessary for Growth on Glucose," *Yeast*, 1992, pp. 183-192, vol. 8. John Wiley & Sons Ltd.

Hauf, Jörg, et al., "Simultaneous genomic overexpression of seven glycolytic enzymes in the yeast *Saccharomyces cerevisiae*," *Enzyme and Microbiol Technology*, 2000, pp. 688-698, vol. 26.

Heinisch, Jürgen, et al., "A Yeast Phosphofructokinase Insensitive to the Allosteric Activator Fructose 2,6-Bisphosphate," *The Journal of Biological Chemistry*, Jul. 5, 1996, pp. 15928-15933, vol. 271, No. 27.

Kasahara, Michihiro, et al., "Amino Acid Residues Responsible for Galactose Recognition in Yeast Gal2 Transporter," *Journal of Biological Chemistry*, Jul. 4, 1997, pp. 16721-16724, vol. 272, No. 27. The American Society for Biochemistry and Molecular Biology, Inc.

Kasahara, Michihiro et al., "Contribution to Substrate Recognition of Two Aromatic Amino Acid Residues in Putative Transmembrane Segment 10 of the Yeast Sugar Transporters Gal2 and HXT2," *The Journal of Biological Chemistry*, Oct. 30, 1998, pp. 29106-29112, vol. 273, No. 44.

Kasahara, Michihiro, et al., Transmembrane segment 10 is important for substrate recognition in GAl2 and Hxt2 sugar transporters in the yeast *Saccharomyces cerevisiae, FEBS Letters*, Jul. 1, 1996, pp. 174-178, vol. 389, No. 2.

Kasahara, Toshiko et al., "Interaction between the critical amino acid residues $Tyr^{352}$ and $Phe^{504}$ in the yeast Gal2 transporter," FEBS Letters, Apr. 2000, pp. 103-107, vol. 471. Federation of European Biochemical Societies.

Kasahara, Toshiko, et al., "Three Aromatic Amino Acid Residues Critical for Galactose Transport in Yeast Gal2 Transporter," *Journal of Biological Chemistry*, Feb. 11, 2000, pp. 4422-4428, vol. 275, No. 6. The American Society for Biochemistry and Molecular Biology, Inc.

Ko, Christopher H., et al., Roles of Multiple Glucose Transporters in *Saccharomyces cerevisiae, Molecular and Cellular Biology*, Jan. 1993, pp. 638-648, vol. 13, No. 1. American Society for Microbiology.

Kruckeberg, Arthur L., "The hexose transporter family of *Saccharomyces cerevisiae,*" *Arch. Microbiol.*, 1996, pp. 283-292, vol. 166.

Larsson, Christer, et al., "Glycolytic Flux Is Conditionally Correlated with ATP Concentration in *Saccharomyces cerevisiae*, a Chemostat Study under Carbon- or Nitrogen-Limiting Conditions," *Journal of Bacteriology*, Dec. 1997, pp. 7243-7250, vol. 179, No. 23. American Society for Microbiology.

Larsson, Christer, et al., The importance of ATP as a regulator of glycolytic flux in *Saccharomyces cerevisiae, Yeast*, 2000, pp. 797-809, vol. 16.

Larsson, Christer, et al., "The Importance of the Glycerol 3-Phosphate Shuttle During Aerobic Growth of *Saccharomyces cerevisiae,*" *Yeast*, 1998, pp. 347-357, vol. 14, No. 4.

Lewis, Deborah A., et al., "The *HXT1* Gene Product of *Saccharomyces cerevisiae* Is a New Member of the Family of Hexose Transporters," *Molecular and Cellular Biology*, Jul. 1991, pp. 3804-3813, vol. 11, No. 7. American Society for Microbiology.

Meijer, Michelle, et al., "Glucose Repression in *Saccharomyces cerevisiae* Is Related to the Glucose Concentration Rather Than the Glucose Flux," *The Journal of Biological Chemistry*, Sep. 11, 1998, pp. 24102-24107, vol. 273, No. 37. The American Society for Biochemistry and Molecular Biology, Inc.

Mueckler, Mike, "Facilitative glucose transporters," *Eur. J. Biochem.*, 1994, pp. 713-725, vol. 219.

Nishizawa, Kazuhisa, "Substrate Recognition Domain of the Gal2 Galactose Transporter in Yeast *Saccharomyces cerevisiae* as Revealed by Chimeric Galactose-Glucose Transporters," *Journal of Biological Chemistry*, Feb. 10, 1995, pp. 2423-2426, vol. 270, No. 6. The American Society for Biochemistry and Molecular Biology, Inc.

Özcan, Sabire et al., "Function and Regulation of Yeast Hexose Transporters," *Microbiology and Molecular Biology Reviews*, Sep. 1999, pp. 554-569, vol. 63, No. 3. American Society for Microbiology.

Özcan, Sabire, et al., "Glucose sensing and signaling by two glucose receptors in the yeast *Saccharomyces cerevisiae*," *The EMBO Journal*, 1998, pp. 2566-2573, vol. 17, No. 9.

Özcan, Sabire, et al., "Two glucose transporters in *Saccharomyces cerevisiae* are glucose sensors that generate a signal for induction of gene expression," *Proc. Natl. Acad. Sci. USA*, Oct. 1996, pp. 12428-12432, vol. 93.

Pao, Stephanie S., et al., "Major Facilitator Superfamily," *Microbiology and Molecular Biology Reviews*, Mar. 1998, pp. 1-34, vol. 62, No. 1. American Society for Microbiology.

Reifenberger, E., et al., Identification of novel *HXT* genes in *Saccharomyces cerevisiae* reveals the impact of individual hexose transporters on glycolytic flux, *Molecular Microbiology*, Apr. 1995, pp. 157-167, vol. 16, No. 1. Blackwell Science Ltd.

Reifenberger, Elke, et al., "Kinetic characterization of individual hexose transporters of *Saccharomyces cerevisiae* and their relation to the triggering mechanisms of glucose repression," *Eur. J. Biochem.*, Apr. 1997, pp. 324-333, vol. 245, No. 2.

Sherwood, Peter W., "A Glucose Transporter Chimera Confers a Dominant Negative Glucose Starvation Phenotype in *Saccharomyces cerevisiae,*" *Genetics*, Jun. 2000, pp. 989-992, vol. 155.

Teusink, Bas, et al., "Intracellular Glucose Concentration in Derepressed Yeast Cells Consuming Glucose is High Enough to Reduce the Glucose Transport Rate by 50%," *Journal of Bacteriology*, Feb. 1998, pp. 556-562, vol. 180, No. 3. American Society for Microbiology.

Thevelein, Johan M., et al., "Trehalose synthase: guard to the gate of glycolysis in yeast," *Trends Biochem Sci.*, 1995, pp. 3-10, vol. 20.

Van Aeist, Linda, et al., "Molecular cloning of a gene involved in glucose sensing in the yeast *Saccharomyces cerevisiae*," *Molecular Microbiology*, 1993, pp. 927-943, vol. 8, No. 5.

Van Dijken, J. P., et al., "An interlaboratory comparison of physiological and genetic properties of four *Saccharomyces cerevisiae* strains," *Enzyme and Microbiol Technology*, 2000, pp. 706-714, vol. 26. Elsevier Science Inc.

Visser, Wiebe, et al., "Oxygen Requirements of Yeasts," *Applied and Environmental Microbiology*, Dec. 1990, pp. 3785-3792, vol. 56, No. 12. American Society for Microbiology.

Walsh, Michael, et al., "Affinity of Glucose Transport in *Saccharomyces cerevisiae* Is Modulated during Growth on Glucose," *Journal of Bacteriology*, Feb. 1994, pp. 953-958, vol. 176, No. 4.

Wieczorke, Roman, Concurrent knock-out of at least 20 transporter genes is required to block uptake of hexoses in *Saccharomyces cerevisiae, FEBS Letters*, 1999, pp. 123-128, vol. 464.

Ye, Ling, "Growth and Glucose Repression Are Controlled by Glucose Transport in *Saccharomyces cerevisiae* Cells Containing only One Glucose Transporter," *Journal of Bacteriology*, Aug. 1999, pp. 4673-4675, vol. 181, No. 15. American Society for Microbiology.

Fell, "Conclusion," in *Understanding the Control of Metabolism*, 1997, pp. 255-277, Portland Press, London, UK and Miami, FL.

Hohmann, "Pyruvate Decarboxylases," 1997, pp. 187-211, in *Yeast Sugar Metabolism. Biochemistry, Genetics, Biotechnology and Applications*, Zimmermann and Entian (Eds.), Technomic Publishing Co., Inc., Lancaster, PA.

* cited by examiner

RECOMBINANT *SACCHAROMYCES CEREVISIAE* EXPRESSING CHIMERIC GLUCOSE TRANSPORTERS

This application is a National Phase of International Application Serial No. PCT/GB01/03079, filed Jun. 29, 2001.

The present invention relates to a yeast having modified saccharide, particularly hexose, transporting properties and its use.

The purpose of the invention is to obtain a yeast having modified saccharide, particularly hexose transporting properties while simultaneously avoiding production of alcohol, in particular ethanol under aerobic conditions and high saccharide, particularly hexose concentrations.

Yeast glycolysis, the pathway which converts sugar into pyruvate, has a massive capacity as has been documented by the fact that 50-70% of the yeast's cellular protein consists of glycolytic enzymes. Not surprisingly, this pathway is controlled in a very complex way and by different partially redundant mechanisms (Fraenkel, 1982, Carbohydrate metabolism, p. 1-37, in "The molecular biology of the yeast *Saccharomyces cerevisiae*: Metabolism and gene expression" Cold Spring Harbor Laboratory, Cold Spring Harbor, N.Y.; Gancedo and Serrano, 1989, Energy-yielding metabolism, p. 205-259, in "The Yeasts", Rose and Harrison (Eds.), Second ed, vol. 3. Academic Press; Zimmermann and Entian, 1997, Yeast sugar metabolism, in "Biochemistry, genetics, biotechnology and applications.", Technomic Publishing Co., Lancaster Pa.). Some of these seem to be shared with glycolytic pathways from other organisms up to humans and higher plants, but others appear to be unique to yeast.

Regulation of yeast glycolysis occurs via allosteric control of key enzymes in the pathway such as phosphofructokinase (PFK) and pyruvate kinase (Blazquez et al., 1993, FEBS Lett., 329, p51-54; Boles et al., 1996, Mol. Microbiol., 20, p65-76; Campbell-Burk and Shulman, 1987, Ann. Rev. Microbiol., 41, p595-616; Davies and Brindle, 1992, Biochemistry, 31, p4729-4735; Gancedo and Serrano, 1989, supra; Heinisch et al., 1996, J. Biol. Chem., 271, p15928-15933). For a long time PFK was considered to be the (single) rate-limiting step in glycolysis. The development of metabolic control analysis theory has shown this to be an oversimplification (Fell, 1997, in "Understanding the Control of Metabolism", Portland Press, London and Miami).

A control mechanism which is probably specific to yeast but of central importance, operates at the level of hexokinase and involves trehalose metabolism (Thevelein and Hohmann, 1995, Trends Biochem. Sci., 20, p3-10). Inactivation of trehalose-6-phosphate synthase causes an absence of trehalose accumulation, but also a growth defect, specifically when grown on glucose (González et al., 1992, Yeast, 8, p183-192; Van Aelst et al., 1993, Mol. Microbiol., 8, p927-943). The expression of heterologous trehalose-6-phosphate synthase in a mutant of *S. cerevisiae* lacking the same enzyme restored trehalose-6-phosphate levels as well as growth on glucose and glucose influx, at least partially (Bonini et al., 2000, Biochemical Journal, 15, p261-268).

Also other metabolites and/or co-metabolites such as ATP, ADP, NAD+ and Pi, may be involved at different levels such as allosteric control and the so-called "thermodynamic control" (alternatively "concentration" or "metabolite control") (Gancedo and Serrano, 1989, supra). A strong "negative" correlation between the ATP content and glycolytic flux has been found, which points at an allosteric control of flux. In a recent study it has been shown that the target for ATP inhibition in permeabilised cells was mainly at the level of phosphofructokinase and pyruvate kinase (Larsson et al., 2000, Yeast, 16, p797-809).

Altering expression of genes encoding glycolytic enzymes and proteolysis of glycolytic enzymes are other levels of regulation and control, which is far from understood when considering glycolytic control (Hohmann, 1997, p 187-211, in "Yeast sugar metabolism. Biochemistry, genetics, biotechnology and applications", Zimmermann and Entian (Eds.), Technomic Publishing Co. Inc., Lancaster, Pa.; Larsson et al., 1997, J. Bacteriol., 179, p7243-7250).

The yeast *S. cerevisiae* has a remarkable metabolic flexibility and it is one of the few yeasts which is able to grow fermentatively under strict anaerobic conditions (Visser et al., 1990, Appl. Environ. Microbiol., 56(12), p3785-3792). During aerobic conditions and with simultaneously relatively high external glucose concentrations, the Crabtree effect is exerted, which results in ethanol production also during aerobic growth on fermentable sugars (Fraenkel, 1982, supra; Gancedo and Serrano, 1989, supra). A number of causes of the Crabtree effect have been put forward. Firstly, it has been suggested that increased extracellular (or intracellular) levels of glucose cause repression of the activity of key elements of the respiratory pathway leading instead to processing via the fermentation pathway. Alternative explanations suggest that the effect may simply occur through overload of the glycolytic pathway leading to a shunt of carbon sources to fermentative processes.

As mentioned above, glucose repression (=(carbon) catabolite repression) may be part of the explanation for aerobic ethanol production during growth on fermentable sugars (Fraenkel, 1982, supra; Gancedo and Serrano, 1989, supra; Gancedo, 1992, Eur. J. Biochem., 206, p297-313). The primary effect of glucose repression is that glucose and fructose are the preferred carbon sources if a mixture of different sources is available. There is a whole series of genes involved in glucose repression and the extent of repression is correlated with the glucose uptake capacity. This suggests that the rate of glucose utilisation determines the strength of the relevant glucose signal (Gancedo, 1998, Microbiol. Mol. Biol. Rev., 62, p334-361).

However, it has been proposed that the extracellular (or intracellular) glucose concentration, rather than the glucose flux, triggers glucose repression (Meijer et al., 1998, J. Biol. Chem., 273, p24102-24107). If the glucose is sensed inside the cell then the transporters may have an indirect role not only in the generation of the initial signal but also in the maintenance of such a signal (Reifenberger et al., 1997, Eur. J. Biochem., 245, p324-333; Walsh et al., 1994, J. Bacteriol., 176, p953-958).

The intracellular glucose concentration has recently been shown to be much higher than reported previously, i.e. around 1.5 mM. This concentration is sufficient to reduce glucose influx by 50% (Teusink et al., 1998, J. Bacteriol., 180, p556-562). The authors of this study concluded that intracellular glucose is a strong candidate for regulation of glucose import and hence glycolysis.

During different external sugar concentrations, yeast cells exhibit high ($K_m$ approx. 1-3 mM) or low ($K_m$ approx. 10-50 mM) affinity sugar uptake systems (Bisson and Fraenkel, 1983, Proc. Natl. Acad. Sci. USA, 80, p1730-1734; Walsh et al., 1994, supra). Cells growing in low glucose media often display both a high affinity component and a low affinity component (Bisson and Fraenkel, 1983, supra). Glucose is transported into the yeast cell by facilitated diffusion through different specific carrier proteins (Bisson et al., 1993, Crit. Rev. Biochem. Mol. Biol., 28, p259-308).

Genetic studies have implicated a gene family, the HXT-family, including 20 homologous genes in encoding hexose transporters (Kruckeberg, 1996, Arch. Microbiol., 166, p283-292; Diderich et al., 1999, J. Biol. Chem., 274, p15350-15359; Ozcan and Johnston, 1999, Microbiol. Mol. Biol., 63, p554-569). The HXT family belongs to the major facilitator superfamily (Pao et al., 1998, Microbiol. Mol. Biol. Rev., 62, p1-34). Different members of the family are expressed to different levels depending on the external glucose concentration (Diderich et al ., 1999, supra). HXT1 is induced by high glucose concentrations, whereas HXT2, HXT4, and HXT6-7 are induced at low glucose concentrations and HXT3 is induced irrespective of glucose concentration. Furthermore, transcription of HXT1-7 is correlated to the extracellular glucose concentration. Also other conditions, such as nitrogen availability and aerobicity/anaerobicity affect the expression of members of the HXT family (Reifenberg et al., 1995, Mol. Microbiol., 16, p157-167; Reifenberger et al., 1997, supra; Diderich et al., 1999, supra).

The HXT family also includes GAL2 that encodes a galactose transporter, which also transports glucose, and SNF3 and RGT2, encoding putative sensors of high and low glucose concentrations, respectively (Diderich et al., 1999, supra; Ozcan and Johnston, 1999, supra). The putative sensor proteins probably serve as glucose receptors and contains unusually long C-terminal tails that are predicted to be in the cytoplasm (Ozcan et al., 1996, Proc. Natl. Acad. Sci. USA, 93, p12428-12432; Ozcan et al., 1998, EMBO. J., 17, p2566-2573)

Modification of *Saccharomyces cerevisiae* by constructing DNA constructs which comprise a HXT-gene, in particular by using HXT1 and/or HXT3-genes, for increasing the production of ethanol, in particular for producing alcoholic beverages and liquor, is previously known from EP-A-0 785 275.

However, Saccharomyces yeast that produce little or no alcohol under aerobic conditions whilst still exhibiting growth, are not known.

For several thousands of years yeast has been used for the preparation of alcoholic beverages and in the future this process might become even more important for the production of ethanol as a renewable fuel. However, many more products other than alcohol can potentially be produced by yeast from renewable resources. For example other valuable substances such as fine chemicals, non-alcoholic drinks and homologous and/or heterologous compounds such as proteins or low molecular metabolites could, and in many cases, are produced.

In order to compete successfully with production processes based on other techniques, e.g. using fossil raw material (such as oil, which may be used as the basis for producing some products, e.g. fine chemicals), the highest possible yield is required. A potential problem is that "good" carbon sources such as glucose often cause repression of genes required for synthesis of the desired substance. As a result the yield will be low or the product may not even be formed. To overcome, or at least minimise, these effects different cultivation techniques such as fed-batch cultivation or growth in a chemostat is often employed, which avoids general increases in the concentration of the carbon source, e.g. glucose, which could lead to repression.

It has however now surprisingly been found that by appropriate modification of the saccharide transport capabilities of the yeast, processing through the fermentation pathway of *Saccharomyces cerevisiae* can be avoided, even in the presence of high concentrations of saccharide as the carbon source, e.g. fermentable sugars such as glucose, but with maintenance of good growth and carbon source consumption. No other workers in the field have produced yeast with such advantageous properties.

The present invention thus offers a solution to the existing problems of processing through the fermentative pathway under aerobic conditions and high saccharide levels since the yeasts containing the constructs of the invention seem to be relieved from the Crabtree effect, e.g. relieved from glucose repression. Hence, if fermentation is largely absent (e.g. via the absence of glucose repression), high yields of different substances can be obtained without resorting to sophisticated cultivation techniques.

The present invention thus relates to non-ethanol producing strains of *Saccharomyces cerevisiae* having specific hexose transporting properties, whereby changes in the hexose transporting gene provides one way of obtaining said non-ethanol producing property.

The invention described herein thus particularly relates to a chimeric construct between saccharide, e.g. glucose and/or galactose (preferably glucose), transporters, especially preferably between a high (for example HXT7) and a low (for example HXT1) affinity hexose transporter of the yeast *S. cerevisiae*.

Apart from traditional processes such as baker's yeast production, the industrial applications also include production of homologous and/or heterologous substances such as proteins or low molecular metabolites, as well as bulk and fine chemicals, food stuffs including yeast extracts, functional food and therapeutic agents. Another application area is the production of fermented non-alcoholic beverages.

Thus in a first aspect the present invention provides a modified *Saccharomyces* yeast which produces lower levels of alcohol, in particular ethanol, than wild-type yeast under aerobic conditions and saccharide concentrations of 5 mM or more, preferably 2% glucose, and which exhibits a growth rate of at least 30% of the wild-type yeast.

Alternatively stated, the present invention provides a *Saccharomyces cerevisiae* strain having modified hexose transporting properties, which is non-ethanol producing under aerobic growth and high hexose concentrations. Preferably said *Saccharomyces cerevisiae*, has heterologous and/or homologous expressed substances as described hereinafter.

Preferably, said yeast produces less than 50%, e.g. less than 30, 20 or 10% alcohol (particularly ethanol), especially preferably less than 5%, e.g. less than 3, 2 or 1% alcohol (particularly ethanol) compared to wild-type. Conveniently, this may correspond to alcohol (preferably ethanol) levels less than 0.6 g/l, e.g. less than 0.25 g/l, especially preferably, less than or equal to 0.15 g/l, e.g. less than or equal to 0.12 g/l, under the conditions of assay.

Preferably, said yeast exhibits a generation time of at least 30%, 35, 40, 45, 50, 60, 70 or 80% (preferably at least 60, 70 or 80%) relative to wild-type yeast, e.g. a generation time of less than 4.5 h, e.g. less than 3.9, 3.5 or 3.0 h or an equivalent growth rate.

In a particularly preferred feature therefore, the present invention provides a modified *Saccharomyces* yeast which produces less than or equal to 0.15 g/l alcohol (in particular ethanol) under aerobic conditions and saccharide concentrations of 5 mM or more, preferably 2% glucose, and which exhibits a growth rate of more than 50% of the wild-type yeast.

The modified yeast of the invention may exhibit reduced glucose consumption, e.g. less than 50%, e.g. less than or equal to 40% less than wild-type yeast, e.g. less than 5 mmol glucose/(g biomass.h), but preferably consumes more than 20%, e.g. more than 30, 40 or 50% compared to wild-type.

Preferably the growth yield of the yeasts of the invention is at least 30%, e.g. from 30 to 120%, e.g. more than 40 or 50%, preferably more than 60, 80 or 100% of the wild-type yeast, e.g. more than 0.20, e.g. more than 0.35, 0.40 or 0.50 g biomass/g glucose.

Preferably the oxygen consumption of yeasts of the invention is improved relative to wild-type yeast, ie. is at least 100%, preferably at least 150, 175 or 200% relative to wild-type yeast, e.g. more than 2, 2.5, 3 or 4 mmol $O_2$/(g biomass.h).

Especially preferably the yeasts of the invention exhibit modified saccharide, e.g. hexose, e.g. glucose transporting properties. The transport of other saccharides, particularly galactose and/or maltose may also be affected.

Alteration of the saccharide transporting properties of yeast is conveniently achieved by introducing exogenous molecules related to naturally occurring transport molecules. Especially preferably chimeric constructs between portions of known transporter molecules may be generated and incorporated into yeast cells and thereby affect their trafficking of saccharides and their use of the respiratory and fermentation pathways under aerobic conditions.

The Hxt-family and other saccharide transporters have very similar topology and are proteins with 12 transmembrane domains. It has now been found that combining portions from different molecules provides functional transporter molecules which exhibit altered transporting properties. Without wishing to be bound by theory, it appears that such chimeras result in glucose derepression thus leading to enhanced use of the respiratory pathway and thus reduced alcohol production.

As described hereinafter in more detail, various chimeric molecules have been produced and integrated into the genome of *Saccharomyces cerevisiae*. In particular the development and testing of 2modified yeast are described which contain chimeric constructs between portions of HXT1 and HXT7.

In the case of the first modified yeast (KOY.TM6 also referred to herein as KOY.TM6P), the fusion between the two genes has been effected in the region encoding transmembrane region 6 (TM6). This strain, KOY.TM6P, shows derepressed properties during growth on glucose in the presence of oxygen i.e. only minute amounts of ethanol are formed (less than 0.12 g/l during growth on 2% Glucose). Simultaneously, a relatively high growth rate with a generation time of 3.8 h, sugar consumption rate 3.1-3.9 mmol/(g biomass.h) and growth yield of 0.41 g biomass/g glucose is obtained.

The second modified yeast, KOY.TM4 (also referred to herein as KOY.TM4P) contains a construct in which the genes have been attached in the region encoding transmembrane region 4. This modified yeast shows growth properties very similar to those seen for KOY.TM6. It has a growth rate with a generation time of 3 to 3.9 h and a yield of 0.34 g biomass/g of glucose.

Thus, in a preferred feature, yeasts of the invention contain a chimeric nucleotide sequence (a chimeric construct), preferably as defined hereinbelow, which is stably transformed into the genetic material of the yeast, wherein the construct comprises 2 or more nucleic acid sequences encoding different saccharide, e.g. glucose and/or galactose (preferably glucose), transporters, ie. the construct comprises at least a first sequence from the nucleotide sequence encoding a first saccharide transporter (or a sequence related to or derived therefrom) and a second sequence from the nucleotide sequence encoding a different second saccharide transporter (or a sequence related to or derived therefrom), wherein said saccharide is preferably glucose.

Especially preferably the construct is between at least a high and a low affinity hexose transporter, preferably of the yeast *Saccharomyces*, preferably *Saccharomyces cerevisiae*, which form said first and second saccharide transporters as described above. Preferably the transporters are selected from HXT1 to HXT17, GAL2, SNF3, RGT2, AGT1, YDL247w and YJR160c, preferably from *Saccharomyces cerevisiae* or sequences related to or derived from the sequences of such molecules. In particular, analogous and related sequences from other species or genera, e.g. from bacteria, plants or animals, may be used to produce the chimeras.

Thus, the present invention preferably provides a *Saccharomyces cerevisiae* as described herein, comprising any combination of one or more of functional hexose transporters of the group HXT1 to HXT17, GAL2, SNF3, RGT2. AGT1, YDL247w and YJR160c. Especially preferably, said *Saccharomyces cerevisiae* comprises any combination of one or more of functional hexose transporters of the group HXT1 to HXT7.

The amino acid sequences of such molecules are as described in P32465 (HXT1) [SEQ ID NO: 22], P23585 (HXT2) [SEQ ID NO: 23], P32466 (HXT3) [SEQ ID NO: 24], P32467 (HXT4) [SEQ ID NO: 25], P38695 (HXT5) P39003 (HXT6) [SEQ ID NO: 26], P39004 (HXT7) [SEQ ID NO: 27], S50771 (HXT8) S50708 (HXT9) S48313 (HXT10) S49600 (HXT1 1) S50356 (HXT12) S50520 (HXT13) S63299 (HXT14) S67809 (HXT15) S57187 (HXT16) S63405 (HXT17) P13181 (GAL2) [SEQ ID NO: 28], A31928 (SNF3) S67684 (RGT2) S64624 (AGT1) S67812 (YDL247w) and S57190 (YJR160c) in which the accession numbers prefixed with S or A refer to those from the PIR Database and those prefixed with P refer to those from the Swiss-Prot database.

Also included within the scope of the invention are chimeras made from one or more sequences related to or derived from the above described amino acid sequences (or chimeric constructs made from the nucleotide sequences encoding one or more sequences related to or derived from the above described sequences)., e.g. one (or more) naturally occurring sequence may be combined with a sequence derived from a different naturally occurring molecule or a combination between 2 (or more) sequences each related to a different molecule may be used.

Especially preferably, the nucleotide sequence encoding a chimera of, or for use in, the invention, may comprise
  one or more sequences or portions thereof (particularly as described hereinbelow) of the sequences encoding any one of HXT1 to HXT17, GAL2, SNF3, RGT2, AGT1, YDL247w and YJR160c, preferably from *Saccharomyces cerevisiae*, as described above,
    or a sequence which hybridizes to said sequence or portion thereof under non-stringent binding conditions of 6×SSC/50% formamide at room temperature and washing under conditions of high stringency, e.g. 2×SSC, 65° C., where SSC=0.15 M NaCl, 0.015M sodium citrate, pH 7.2,
    or a sequence which exhibits at least 80%, preferably 90 or 95% e.g. at least 98% sequence identity to said sequence or portion thereof (as determined by, e.g. FASTA Search using GCG packages, with default values and a variable pamfactor, and gap creation penalty set at 12.0 and gap extension penalty set at 4.0 with a window of 6 nucleotides),
  or a sequence complementary to any of the aforesaid sequences.

Such sequences or portions thereof may comprise a first or second sequence as described hereinbelow.

"Portions" as referred to above, preferably comprise at least 30% of the wild-type sequence, e.g. at least 50, 70 or 90% of the sequence, e.g. comprise 300 or more bases, preferably 500 or more or 600 or more bases. However shorter portions may also be contemplated when chimeras are made up of multiple portions. In such case the portion may have for example 50 to 200 bases. Portions as referred to in connection with amino acid sequences comprise comparable lengths as those encoded by the above described nucleotide sequences, e.g. 100 or more residues, preferably more than 180 or 200 residues, or shorter portions such as 15 to 65 residues.

Alternatively viewed, especially preferably the nucleotide sequences encoding a chimera of, or for use in, the invention, encodes an amino acid sequence which may comprise
- one or more sequences or portions thereof (particularly as described hereinbelow) of the sequences of any one of HXT1 to HXT17, GAL2, SNF3, RGT2, AGT1, YDL247w and YJR160c, preferably from *Saccharomyces cerevisiae*, as described above,
- or a sequence which exhibits at least 80%, preferably 90 or 95% e.g. at least 98% sequence identity to said sequence or portion thereof (as determined by, e.g. using the SWISS-PROT protein sequence databank using FASTA pep-cmp with a variable pamfactor, and gap creation penalty set at 12.0 and gap extension penalty set at 4.0, and a window of 2 amino acids).

Such sequences or portions thereof are encoded by a nucleotide sequences which may comprise a first or second sequence as described hereinbelow.

Preferably, where the nucleic acid sequences used to make the chimeras are related to or derived from the naturally-occurring sequences (and preferably fall within the above described families), the related or derived sequences encode a functionally equivalent protein or precursor or portion thereof.

Preferably therefore, the invention extends to a *Saccharomyces cerevisiae* as defined above, comprising any combination of one or more functional hexose transporters genes, the DNA sequences being derived from these genes by substitution, deletion, or addition of one or more nucleotides in such a way that the DNA sequence still encodes a protein capable of transporting hexose(-s)., e.g. glucose.

The invention also extends to chimeric constructs encoding proteins which are functionally equivalent to those described above and below, e.g. which are formed by combination of naturally-occurring molecules (or sequences related to or derived therefrom, e.g. functional equivalents), wherein that combination may be further modified, e.g. by substitution, deletion or addition, to provide a sequence encoding a functionally equivalent protein or precursor or portion thereof as defined hereinbelow, wherein preferably said functionally-equivalent protein satisfies the identity defined above, e.g. has at least 98% identity to the sequence formed by the combination, or wherein the encoding sequence satisfies the identity or hybridizing conditions described above.

Thus in a further feature the invention provides a modified recombinant *Saccharomyces cerevisiae* as described herein expressing a modified gene (e.g. a chimeric construct as described herein) deriving from the genes of any one of the saccharide transporters described herein, preferably EXT1 and HXT7, or derived transformants (e.g. functionally equivalent nucleic acid molecules) thereof.

Thus the present invention provides a nucleotide sequence comprising a chimeric nucleotide sequence as described herein or a functionally equivalent nucleic acid molecule thereto, preferably satisfying the identity and/or hybridizing conditions described above, and modified yeast cells containing the same.

Preferably chimeras are made between low affinity transporters, preferably HXT1 or HXT3 and high affinity transporters, preferably HXT2, 4, 6, 7 (especially preferably HXT6 or 7) or GAL2P.

Particularly preferably chimeric constructs are made between HXT1 and HXT7 or sequences related to or derived therefrom, and used to transform yeast to provide the yeast of the invention. Preferably N-terminal portions of HXT1 are conjugated with C-terminal portions of HXT7, although the alternative form with HXT7 at the N-terminus and HXT1 at the C-terminus is also included within the scope of the invention.

Thus, the nucleotide sequence encoding the chimera (ie. the chimeric construct) comprises a sequence having the form:

A–B wherein
- A is a first component (ie. the first sequence as described hereinbefore) comprising nucleotide bases w to x;
- B is a second component (ie. the second sequence as described hereinbefore) comprising nucleotide bases (x+y) to z;
- wherein A and B are derived from distinct molecules, e.g. HXT1 and HXT7, ie. from the nucleotide sequences of different saccharide transporters or from sequences related to or derived therefrom;
- w is a first position within the nucleotide sequence from which said first component is derived (e.g. HXT1 or HXT7 or a comparable sequence as described above), which is less than x, preferably from 1 to 300, e.g. 1 to 50, especially preferably 1 to 10, e.g. 1;
- x is a second position within the nucleotide sequence from which said first component is derived and is greater than w and is preferably a number from 300 to 1250, e.g. 500 to 850;
- y is an integer, preferably less than 10, e.g. less than 5, e.g. less than 3, e.g. 1;
- x+y is a first position within the nucleotide sequence from which said second component is derived (e.g. HXT1 or HXT7 or a comparable sequence as described above);
- and z is a second position within the nucleotide sequence from which said second component is derived and is greater than x+y, preferably from 800 to 1713, especially preferably 1200 to 1713, e.g. 1600 to 1713, e.g. 1675 to 1713;
- wherein said values refer to the position within the nucleotide sequence of said saccharide transporter, e.g. HXT1 or HXT7 or a comparable sequence thereof.

The transporter molecules of *Saccharomyces cerevisiae* comprise 12 transmembrane sequences. In a preferred feature, the point of junction between the 2 or more portions which together form the chimera falls within the sequence of the 3rd to 9th transmembrane stretches. Thus, preferably x is a position in the sequence encompassed by the third to ninth transmembrane stretches of HXT1 or HXT7 or a comparable sequence, especially preferably 400 to 900, e.g. 525 to 800, for example 525-575 and/or 720-770 especially preferably 545 to 560 and/or 735 to 750 and y is preferably 1 and z is preferably as described above.

Preferably chimeras of the invention have a total of 12 transmembrane domains (e.g. w is less than 10 and x is from 1675 to 1713). This may be achieved by for example combining some of the 12 transmembrane domains (e.g. domains 1 to 3-9, or parts thereof) from a first transporter and the remainder (3-9 to 12, or parts thereof) from a second transporter. However, more or fewer transmembrane domains are also contemplated and linker groups may optionally appear between one or more of the transmembrane domains. Thus, preferably said chimeras of the invention comprise from 6 to 18 transmembrane domains, e.g. 10 to 14, which are derived from 2 or more transporter molecules as described hereinbefore.

Said chimeras described above may contain more than 2 components, e.g. multiple portions, e.g. 2 or more sequences of the nucleotide sequence of one or more transporter molecules or sequences from the nucleotide sequences of more than 2 transporters as described herein, in which case the portions are provided in parallel, preferably to retain the transmembrane structure, e.g. 10-14, preferably 12 transmembrane structure, optionally with one or more linker groups between said portions. A linker group may also be inserted between A and B above (ie. y may be more than 1), providing this does not affect the functionality of the chimera.

Especially preferably x is 551 or 741, w and y=1 and Z=1713. Alternatively, x may be 668. Chimeric polypeptides encoded by such nucleic acid molecules are set forth in Seq. ID Nos. 1 and 2. Such sequences, sequences comprising them, functionally equivalent polypeptides (preferably satisfying the identity requirements described above) and nucleic acid molecules containing a nucleotide sequence encoding the same, form preferred aspects of the invention. In a preferred feature, said encoding nucleic acid sequences are as set forth in Sequence ID Nos. 3 or 4. Yeast cells expressing these forms also form preferred aspects of the invention. In particular, a further aspect of the invention provides a modified recombinant *Saccharomyces cerevisiae* as described above denoted *Saccharomyces cerevisiae* KOY.TM4P or KOY.TM6P or derived transformants thereof, particularly having the deposition number DSM 13832 or DSM 13555, respectively.

Nucleic acid molecules comprising nucleotide sequences as described above, sequences encoding chimeric proteins as described above and complementary sequences thereto form further aspects of the invention. Proteins or polypeptides comprising a sequence. encoded by such nucleic acid molecules form further aspects of the invention. In addition, the invention extends to functionally equivalent proteins as described hereinbefore, in addition to those in which the amino acids have been chemically modified, including by deglycosylation or glycosylation. In particular, these variant proteins may be prepared by postsynthesis/isolation modification of the substrate without affecting functionality, e.g. certain glycosylation, methylation etc. of particular residues. Non-standard amino acid may be used, such as α-aminobutyric acid, penicillamine, pyroglutamic acid or conformationally restricted analogs, e.g. such as Tic (to replace Phe), Aib (to replace Ala) or pipecolic acid (to replace Pro).

Nucleic acid molecules according to the invention may be single or double stranded DNA, cDNA or RNA, preferably DNA and include degenerate, substantially identical and hybridizing sequences as described before. Ideally however genomic DNA or cDNA is employed.

Such exogenous molecules may be introduced into yeast cells by any appropriate means. Suitable transformation or transfection techniques are well described in the literature. The nucleic acid molecules described above may be operatively linked to an expression control. sequence, or a recombinant DNA cloning vehicle or vector containing such a recombinant DNA molecule. In particular, appropriate nucleic acid molecules may be introduced into vectors for appropriate expression in the cell. Alternatively, the naked DNA molecule may be introduced directly into the cell. Conveniently, transformation of yeast cells as described herein is effected by the lithium acetate transformation method (Burke et al., 2000, CSHL Press, p103-105) or by freeze-thaw or spheroplast methods or other appropriate techniques (see e.g. Dohmen et al., 1991, Yeast, 7, p691-692).

Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules of the invention. Appropriate vectors may include plasmids and viruses (including both bacteriophage and eukaryotic viruses). Suitable viral vectors include baculovirus and also adenovirus, adeno-associated virus, herpes and vaccinia/pox viruses. Many other viral vectors are described in the art.

A variety of techniques are known and may be used to introduce the vectors into cells for expression. Such vectors and eukaryotic or prokaryotic cells, particularly yeast cells, into which said vectors have been transfected form further aspects of the invention.

As mentioned above, nucleic acid molecules of the invention, or vectors comprising the same, may be introduced into any eukaryotic or prokaryotic cells, but particularly yeast cells, especially preferably *Saccharomyces cerevisiae*. Such cells may correspond to wild-type cells. However, conveniently, said cells may be modified (e.g. represent an altered recombinant form) even prior to inclusion of the nucleic acid material relating to the chimeric molecules.

Thus in a preferred embodiment, the phenotype of the wild-type cell is modified to produce a null strain in terms of saccharide, particularly glucose, transporting molecules, ie. to provide a null strain without or with severely limited saccharide transporting properties, e.g. exhibiting a glucose uptake preferably less than 2 nmol glucose/min/mg biomass. This may be achieved by modification of the genotype to remove or alter the genes encoding one or more of HXT1-17, Gal2, stl1 and 3 maltose transporters with glucose affinity and transport properties, namely AGT1, YDL247w/MPH2 and YJR160c/MPH3 or by altering the expression of one or more of those genes (e.g. by deleting one or more necessary transcription or translation factors) or by impairing the function of one or more of the expressed transporters. Conveniently, all of the above described genes, control systems affecting these genes or expressed proteins may be altered or impaired such that no active transporters are available for transport. However, alternatively a sub-set of transporters or their genes or expression thereof may be affected, preferably at least HXT1-4,6,7 and GAL2. These effects may be achieved as described above by for example altering the genes of the transporters, by affecting the transcription or translation of the genes, or by dominant negative mutation methodologies. The nucleic acid molecule encoding the chimera as described herein may thereafter be introduced into the null strain to provide a saccharide transporting phenotype.

Constructs and particularly modified *Saccharomyces* strains having the above described properties have great potential as tools for preparative processes in which metabolic pathways can be manipulated and undesirable side-products avoided. A yeast strain that does not produce any ethanol has been sought for a long time. The novel strains will therefore serve as invaluable tools in future efforts of characterization, e.g. to find an explanation for the repression mechanism during aerobic growth on glucose in *S. cerevisiae*. Further, a strain that does not produce any ethanol even when grown on high sugar concentrations during aerobic batch cultivation is also of considerable interest in terms of exploitation for industrial use.

Thus, *Saccharomyces* cells of the invention may be used in any processes in which the production of alcohol and other products produced during fermentation is undesirable. Such processes include for example the production of non-alcoholic high or low molecular metabolites, or low or high molecular weight compounds such as bulk and fine chemicals, food stuffs, functional food, therapeutic agents and non-alcoholic or low alcohol beverages.

These products may be produced by unmodified yeast of the invention, e.g. non-alcoholic or low alcohol beverages may be produced using appropriate saccharide containing carbon sources, e.g. fruit juices. In this way, low or non-alcoholic wines, beers or other drinks may be generated. Non-alcoholic beverages preferably have the alcohol levels defined herein. However, in a preferred feature, a beer is produced with alcohol levels of less than 1% alcohol w/v, especially preferably <0.5%, and similarly wine may be produced with alcohol levels of less than 10%, especially preferably less then 2.5 or 1% alcohol w/v.

Alternatively, such products may be produced by the introduction of exogenous genetic material which encodes a product of interest. Alternatively, exogenous genetic material may be used which influences the metabolic activity of the cell, thus resulting in the production of, or increased production of, a product of the yeast cell, by biasing the metabolic processes of the cell to produce (or increase production of) a desired product. In a further alternative, endogenous genetic material may be modified to influence the metabolic activity of the cell and thus favour production of a desired product.

The products of the above described genetic engineering may occur naturally in said yeast cells prior to genetic engineering, but are made to exhibit improved production after said engineering. In such cases the exogenous material may for example encode a protein involved in the metabolic process (either directly or indirectly), or an inhibitor of a catabolic process, or may provide regulatory control of the expression of such proteins, e.g. an inducible or constitutive promoter.

Modification of endogenous genetic material may be performed to affect a metabolic process, e.g. a sequence encoding a protein or an inhibitor or a sequence providing regulatory control may be modified to thereby effect the functions of that component.

The products of metabolic engineering may however not occur in wild-type yeast, and in which case said engineering may result in expression of one or more polypeptides which is the product, or which makes production of the desired product possible.

In a preferred aspect however, the product is an entity capable of being produced by said yeast cell (prior to inclusion of constructs of the invention) but which is produced in increased quantities after the introduction of exogenous genetic material, or modification of endogenous genetic material, as described above. Thus, in a preferred feature, products which may be produced by yeast of the invention are amino acids, peptides, polypeptides, sugars, small polyols and carbon dioxide, to mention but a few.

Thus, exogenous or endogenous genetic material, encoding a product of interest or part thereof, or a polypeptide which directly or indirectly facilitates production of a product of interest, or exogenous or endogenous genetic material influencing the expression of the same, may be inserted into, or modified in, yeast cells of the invention, e.g. optionally by stable transformation into the cells' genome in the case of exogenous genetic. material. The cells may then be grown under high saccharide concentrations under aerobic conditions and the product thus formed harvested.

Thus, in a yet further aspect the present invention provides a method of inserting exogenous material into a yeast cell as described above, to produce a yeast cell of the invention containing exogenous genetic material, said method comprising at least the steps of introducing said genetic material, preferably contained within a vector, into said cell, e.g. by transformation. Preferably the exogenous material encodes, or controls the expression of, a product which is, or which enables the production of, a product. Alternatively stated the exogenous material encodes said product or portion thereof or encodes a polypeptide (or part thereof) which facilitates the direct or indirect production of said product or portion thereof, or affects the expression of said product or polypeptide. Such a product may be a high or low molecular metabolite, or a low or high molecular weight compound such as a bulk or fine chemical, a food stuff, a functional food or a therapeutic agent, e.g. as described above. Cells obtainable by this method form further aspects of the invention.

These further modified yeast may then be used to produce the desired product which can then be isolated from the yeast cells. Thus in a further aspect the present invention provides the use of a *Saccharomyces cerevisiae* having modified hexose transporting properties and which is non-ethanol producing under aerobic conditions and high hexose concentrations, in the preparation and manufacture of substances including low or high molecular weight metabolites, preferably in the preparation and manufacture of bulk and fine chemicals, food stuffs, functional food, therapeutic agents or non-alcoholic beverages.

Alternatively viewed the invention further provides a method of preparing a product, e.g. a polypeptide, amino acid, sugar or polyol in a yeast of the invention containing the genetic material as described above, said method comprising growing said yeast cells under aerobic conditions in the presence of high saccharide, preferably glucose, concentrations. In an alternative preferred feature, as mentioned above, products are produced by yeasts of the invention which have not been further modified, but which produce low levels of alcohol and thus when grown on an appropriate medium produce products of interest, e.g. low or non-alcoholic beverages. In a preferred feature the products thus produced as described above are isolated and form further aspects of the invention.

In determining the growth, alcohol production, saccharide consumption or other parameters described herein the following test conditions are used. These parameters are assessed during the period of exponential growth under aerobic ($O_2$ non-limiting) conditions at 30° C., in the medium used by Verduyn et al. (1992, Yeast, 8, p501-517) at pH 5.00 in the presence of 2% glucose, with a starting culture of 0.3 to 0.7 g dry biomass/l (preferably 0.3) in 1.5l fermentors, stirred at 1500 rpm and an air inflow of 0.5 volume of air per vessel volume per minute (vvm)

Biomass content (dry weight) is determined as follows: 5 ml is removed from the culture and centrifuged for 5 minutes in pre-weighed dry weight tubes at sufficient rpm to pellet substantially all the cells. The pellet is washed once with 5 ml 0.9% NaCl and re-pelleted. The pellet is dried for 24 hours at 110° C. before temperature equilibration and weighing.

Continuous gas analysis is effected using a carbon dioxide and oxygen monitor type 1308, Bruel and Kjaer, Naerum, Denmark, e.g. to calculate oxygen consumption rates.

Glucose and ethanol determinations are made in the samples as follows: 1.5 ml samples of the culture are centrifuged at 15000 g for 1 minute and the resulting supernatants frozen at −20° C. until analysis. Concentrations are determined using enzyme combination kits from Boehringer Mannheim, GmbH, Germany.

As used herein, a "modified" yeast refers to one which has been derived from or is related to a wild-type yeast but exhibits phenotypic and preferably also genotypic variation thereto. Preferably the genotype has been modified, particularly in relation to genes encoding saccharide transporting molecules, which results in an altered phenotype. Conveniently this may be achieved by recombination to remove and/or modify existing genetic information and/or alter and/or integrate exogenous genetic sequences. Preferably the modification relates to at least the inclusion of chimeric nucleic acid molecules as described herein. Additional modifications may however also be contemplated, preferably those which further affect the saccharide transporting molecules, e.g. by the creation of yeast cells which are unable to transport glucose or exhibit a severely restricted capacity to do so, prior to insertion of the chimera. These recombinant organisms form preferred features of the invention. Furthermore, additional genetic modifications may be contemplated, e.g. to introduce genetic material encoding a desirable product or portion thereof.

As used herein "wild-type" refers to the yeast strain from which the modified yeast is originally derived or to which it is related. When reference is made to % alcohol, growth etc. of yeast of the invention relative to wild-type, said wild-type refers to the unmodified, naturally occurring, yeast, prior to insertion of constructs of the invention or modification of the genome in any way, ie. does not refer to for example a null strain into which the construct is inserted, but rather refers to the naturally-occurring yeast from which the null strain is generated. Thus when the invention relates to modified *Saccharomyces cerevisiae* yeast, the wild-type is the *Saccharomyces cerevisiae* strain that has been modified. Wild-type sequences refer to those occurring in wild-type microorganisms such as those defined hereinbefore. "Saccharomyces" refers to the genus of the wild-type yeast which is modified. "*Saccharomyces cerevisiae*" refers to the particular species which is preferably modified, and includes all strains falling within that particular species.

As used herein, "alcohol" refers to the production of alcohols such as glycerol and ethanol. However, in the tests described herein, the level of ethanol is tested. Glycerol contributes only a small proportion of the total alcohol content relative to ethanol. "Non-ethanol producing" refers to yeast producing the amounts of ethanol described above, e.g. less than or equal to 0.12 g/l, under the conditions of assay.

The g/l levels of alcohol, in particular ethanol, refers to the amount produced per litre of culture under the test conditions when assessed continually at discrete time points. Maximum levels are generally achieved just prior to glucose depletion during batch cultivation.

"Aerobic conditions" refers to culture conditions which are not limiting for oxygen and thus allow use of respiratory pathways. "Aerobic growth" refers to growth, e.g. as measured by increasing optical density at 610 nm and increase in biomass content under such conditions.

A "transporter" refers to a molecule responsible for transfer of the molecule to be transported from the extracellular culture medium into the cell or vice versa, ie. effecting its passage, e.g. diffusion,. across the plasma membrane. However, in producing chimeras of the invention, saccharide receptors such as SNF3 and RGT2 and sequences related to or derived therefrom may also be used and fall within the scope of the definition of transporters insofar as it relates to transporters which may be used to make chimeras.

"Hexose" or "saccharide" transporting properties refers to the ability of the modified yeast of the invention to take up saccharide from the extracellular culture medium.

A "functional hexose transporter" refers to a transporter molecule which may be a naturally occurring molecule or a functionally equivalent variant as described herein, which is able to transport a saccharide as described above. In reference to functional hexose transporters which may be used to make chimeras of the invention, in line with the definition of transporters, such functional hexose transporters also extend to molecules which have the function of saccharide receptors.

By "hexose transporter gene" is meant a gene encoding a protein which effects the passage, e.g. diffusion, of hexoses across the plasma membrane, for example the HXT4, HXT5, or HXT6 genes.

"Saccharide" refers to mono-, di- or poly-saccharides which may be used as a carbon source by wild-type or modified *Saccharomyces* yeast of the invention. Preferably the saccharides are monosaccharides, particularly preferably glucose, fructose, mannose or galactose, or disaccharides such as maltose. Preferably such saccharides are in the naturally occurring D form. For use under test conditions, naturally occurring underivatized D form saccharides, such as D-glucose, are employed. "Hexose" refers to monosaccharides such as those mentioned above, e.g. glucose, fructose and galactose.

"Growth rate" as referred to herein is mathematically related to generation time and has the relationship: $\mu=\ln(2)/G$; wherein $\mu$ is the specific growth rate, and G is the generation time. As such, values for % generation time rate relative to wild-type yeast similarly provide preferred % growth rates.

"Generation time" is measured in hours and refers to the doubling time, ie. the time taken for each generation to be produced during culture, wherein the generations are assessed by reference to increases in the dry weight of the biomass. Other experiments have been performed which determine generation time by reference to readings at $OD_{610}$. In such cases TM6 yields a value of 2.9 and TM4 a value of 2.5. Definitions provided in the text however refer to the values determined using the dry weight measurement described above.

The "glucose consumption rate", refers to the amount of glucose consumed from the external medium during the test conditions, and is thus assessed by measurement of the glucose in the medium at at least 2 time points and calculation of the glucose consumed in the time between those time points. This value is provided in mmol glucose/(g biomass.h), wherein the g biomass refers to the dry mass of yeast in the culture. "Biomass" refers to the mass attributed to the dry mass of the yeast in the culture.

The term "high hexose" concentrations used in the context of growing the *Saccharomyces cerevisiae* refers to any hexose concentration exceeding 1 mM, preferably exceeding 5 mM present in the media, especially preferably more than 50 mM, e.g. equal to or more than 1 or 2% hexose, preferably glucose. In the test conditions however a value of 2% glucose, ie. 111 mM is used. Similar definitions apply to high saccharide or glucose concentrations. Products as described herein may be produced at various high levels of saccharide, e.g. more than (or equal to) 1, 2, 5, 10 or 20% saccharide. In particular, the higher saccharide levels may be used when producing the beverages described herein.

As used herein, "exponential growth" refers to an exponential rate of doubling the biomass.

As used herein a "chimera" refers to a nucleic acid molecule or polypeptide comprised of two or more sequences (component sequences) derived from two or more different molecules, preferably two sequences each derived from a different molecule. Thus such chimeras provide the result of a combination of such sequences. As described hereinbefore said component sequences (or the parent sequences of which they are a portion) may be naturally occurring or may be related to or derived from such naturally occurring sequences. Whilst conveniently the separate component sequences may be combined together by linking the respective sequences to one another, alternatively, particularly if the sequences are highly homologous, alternative techniques may be used to obtain the chimera, e.g. by mutation of appropriate sites within a particular molecule to arrive at a sequence which in effect reflects a chimera between two distinct sequences.

A "chimeric construct" refers to a nucleic acid molecule comprising at least a nucleotide sequence encoding or providing a chimera as defined above, optionally additionally comprising flanking sequences optionally containing functional elements, e.g. promoter sequences.

"Stably transformed" refers to the inclusion (preferably insertion into the genome) of the construct of the invention into yeast cells as described herein, such that the encoding region of said construct may be expressed, and the construct or part thereof encoding a chimera of the invention is present in the progeny of the yeast cell.

As used herein, "low affinity" transporters refer to those which bind glucose with a $K_m$ of more than 20 mM, e.g. from 50-100 mM under the conditions described herein in Example 1. "High affinity" transporters refer to those having a Km of less than 20 mM, preferably less than 10 mM, e.g. 1-2 mM.

Sequences which are "related to or derived" from nucleotide or amino acid sequences described herein refer to sequences which have been modified relative to those sequences, e.g. by substitution, deletion or addition. Preferably such sequences are functional equivalents as described herein. Especially preferably they have the stated identity or hybridizing properties as described hereinbefore.

"Functionally-equivalent" proteins as used herein refers to proteins related to or derived from the native or naturally-occurring protein, where the amino acid sequence has been modified by single or multiple amino acid substitution, addition and/or deletion, but which nonetheless retain the same function, ie. are capable of transporting (or when used to make chimeras act as a receptor for) one or more saccharide molecules, e.g. glucose, to a lesser or greater extent that the naturally occurring molecules. Such proteins are encoded by "functionally-equivalent nucleic acid molecules" which are generated by appropriate substitution, addition and/or deletion of one or more bases. Preferably the functionally-equivalent protein or nucleic acid molecule satisfies the identity and/or hybridizing conditions as set forth hereinbefore.

Within the meaning of "additions" variants are included amino and/or carboxy terminal fusion proteins or polypeptides, comprising an additional protein or polypeptide fused to the chimeric portion.

Such functionally-equivalent variants mentioned above include natural biological variations (e.g. allelic variants or geographical variations within a species or alternatively in different genera, e.g. plants, animals or bacteria) and derivatives prepared using known techniques. For example, nucleic acid molecules encoding functionally-equivalent proteins may be produced by chemical synthesis or in recombinant form using the known techniques of site-directed mutagenesis including deletion, random mutagenesis, or enzymatic cleavage and/or ligation of nucleic acids. In particular nucleic acid molecules encoding functionally equivalent protein variants for the production of chimeras in accordance with the invention extend to analogues in different genera or species than the specific molecules mentioned herein.

"Precursors" of the naturally occurring proteins may be larger proteins which would be processed, e.g. by proteolysis to yield the substrate. Such precursors may take the form of zymogens, ie. inactive precursors of enzymes, activated by proteolytic cleavage.

"Portions" of functionally equivalent proteins are as described above, and do not themselves necessarily exhibit the activity of the parent molecule. Preferably these portions satisfy the identity (relative to a comparable region) or hybridizing conditions mentioned herein. Portions of products refers to portions which when combined with other entities form the desired product.

"A polypeptide or part thereof which facilitates the direct or indirect production of a product or portion thereof" refers to a molecule, or a part of a molecule or complex, which on expression in a yeast cell of the invention results in the production of the product or part therefore, e.g. by altering or contributing to pathways which affect its production.

A polypeptide "affects the expression" of a product or polypeptide when it exerts a regulatory control on said expression.

The following Examples are given by way of illustration only in which the Figures referred to are as follows.

EXAMPLE 1

Figure 1:
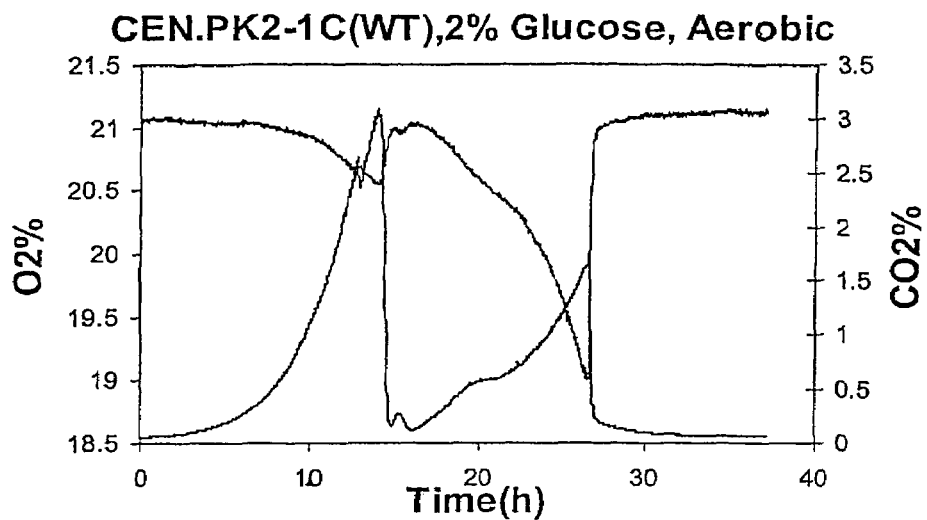
FIG. 1 shows oxygen consumption and carbon dioxide production under different phases of the growth cycle of S. cerevisiae of the prototropic KOY.PK2-1C83 wild-type strain.

Production of Modified *Saccharomyces cerevisiae* Strains Containing Chimeras of HXT1 and HXT7

The yeast HXT-family has clear similarities to the mammalian Glut1. Since this protein has 12 transmembrane domains with N- and C-terminus located in the cytoplasm (Mueckler, 1994, Eur. J. Biochem., 291, p713-725) it is very likely that yeast hexose transporters have similar topology in which the N and C termini are intracellularly located and the sequence joining the termini passes back and forth through the membrane to provide 12 transmembrane regions linked together by intracellular or extracellular loops of various lengths. Chimeras were produced which contained HXT1 at the N-terminus fused together with HXT7 in the transmembrane region. For example, KOY.TM6p (present innovation) which is fused in transmembrane region 6 is identical to HXT1 from the N-terminus up to the middle of transmembrane region 6 while the rest of the protein is equivalent to HXT7.

This gives in total 12 constructs named TM1 to TM12 which have all been integrated into the genome.

Materials and Methods

Strains

A CEN.PK strain with deletions for the genes of the sugar transporters HXT1-7 has been shown to still grow on glucose (Wieczorke et al., 1999, FEBS Lett., 464, p123-128). Because of this the additional HXT genes (altogether 17 genes), as well as further genes (see below) have been deleted in order to obtain a true null strain in terms of glucose transport (Wieczorke et al., 1999, supra)-EBY.VW4000. Although the physiological roles of HXT8-17 have not been described so far (except that HXT9 and 11 have been described to be involved in Multi-Drug-Resistance), they are certainly not silent during all conditions. A hxt5 deletion mutant does not show a clear phenotype in glucose media. It is expressed in glucose deprived cells, probably in order to ensure rapid utilisation of the sugar when it becomes available. The complete null strain is useful, since re-introduction of one or several specific hexose transporter from yeast or even from other organisms can be used to study up-take kinetics and sugar consumption kinetics of specific transporters. Hence, the null strain is in the first place a tool to study the properties of specific yeast or heterologous hexose transporters. The wild-type strain CEN.PK2-1C, has the following genetic markers Mata leu2-52, 112ura3-52, trp1-289, his3-Δ1, MAL2-8c SUC2. This strain was made prototropic (KOY.PK2-1C83) by introducing the marker genes one by one by transformation. The "null mutant" EBY.VW4003 (Mata leu2-52, 112ura3-52, trp1-289, his3-Δ1, MAL2-8c SUC2 HXt1-17Δ, Gal2Δ, Stl1Δ, 3 deleted maltose transporters with glucose affinity, namely AGT1, YDL247w and YJR160c; genomic cassette Pro-HXT7::URA3) is unable to grow on any concentration of glucose. The deletions in the strain to provide the "null strain", which is deleted in all known hexose transporters and putative transporters, was constructed using the lox P/Cre recombinase system (Gueldener et al., 1996, Nucl. Acids Res., 24, p2519). The strain was made prototropic (KOY.VW100) by transformation.

Chimeras

Chimeras between HXTI and HXT7 were made using the PCR based method "in vitro overlap-extension" (Higushi et al., 1981, Nucl. Acids Res., 16, p7351-7367; Ho et al., 1989, Gene, 71, p51-59). The parts to be fused together were first amplified separately but with ends that can anneal with each other. In the second PCR step, flanking primers were used to only allow amplification when annealing of the two separate products had taken place.

For the preparation of TM4, the HXT1 part of TM4 was amplified from plasmid pTHXT1-2 (Reifenberger et al., 1997, supra describes the production of pTHXT1-1 in which the HindIII insert is in the reverse orientation compared to pTHXT1-2) using the following primers:

```
Forward primer:                           (SEQ ID NO: 6)
5'-CAAAGAATAA ACACAAAAAC AAAAAGTTTT TTTAATTTTA
ATCAAAAAAT GAATTCAACT CCCGATCTAA TA-3'

Reverse primer:                           (SEQ ID NO: 7)
5'-GGAGATAAAA CGGCAATACC ACCGACACCT AAACCA-3'
```

The HXT7 part of TM4 was amplified from plasmid P21 (Reifenberger et al., 1995, Mol. Microbiol., 16, p157-167) using:

```
Forward primer:                           (SEQ ID NO: 8)
5'-TGGTTTAGGT GTCGGTGGTA TTGCCGTTTT ATCTCC-3'

Reverse primer:                           (SEQ ID NO: 9)
5'-TTTGTAGACG TGGGTCTGCA GGCA-3'
```

For the preparation of TM6, the HXT1 part of TM6 was amplified from plasmid pTHXTI-2 using the following primers:

```
Forward primer:                           (SEQ ID NO: 10)
5'-CAAAGAATAA ACACAAAAAC AAAAAGTTTT TTTAATTTTA
ATCAAAAAAT GAATTCAACT CCCGATCTAA TA-3'

Reverse primer:                           (SEQ ID NO: 11)
5'-CTGGAACAAA TGTCATACCA CCAATCATAA ATAAGGCCCA
G-3'
```

The HXT7 part of TM6 was amplified from piasmid P21 using:

```
Forward primer:                           (SEQ ID NO: 12)
5'-CTGGGCCTTA TTTATGATTG GTGGTATGAC ATTTGTTCCA
G-3'

Reverse primer:                           (SEQ ID NO: 13)
5'-TTTGTAGACG TGGGTCTGCA GGCA-3'
```

The products from the first two separate reactions were mixed and a PCR run in which the forward primer from the HXT1 reaction and the reverse primer from the HXT7 reaction was used. Since the products from the two first reactions are made in such a way that they have overlapping regions, one obtains a product in which the HXT1 and HXT7 parts are fused together.

The construct KOY.TM6P was made by fusing HXT1 and HXT7 in the sixth trans membrane region, The N-terminus consists of bp 1-741 of HXT1 and the C-terminus of 742-1713 of HXT7. The construct TM4 was made by the same method used f or the TM6 construct but the two genes were fused in TM-region 4. For TM4 this is bp 1-551 of HXT1 and 552-1713 of HXT7.

These constructs were introduced into the KOY.VW100 strain, which was made prototrophic by introducing URA3 prior to said introduction. The cassette used in the null-mutant is located in the former HXT3-6-7 gene cluster and contains the constitutive promoter of HXT7:: K. lactis URA3::HXT7 terminator and was prepared as follows.

Construction of the Genomic Expression Cassette (Sequence ID No.: 5):

A 392 bp HXT7 promoter fragment was integrated into the genome of strain EBY.VW4000 (Wieczorke et al., 1999, supra) into the former HXT3-6-7 gene cluster region by using a modification of the PCR targeting technique, resulting in a very strong and constitutive HXT7 promoter-terminator expression cassette (see Hauf et al., 2000, Enzyme Microb. Technol., 26, p688-698). Part of the HXT7 promoter together with part of the HXT7 coding region from −392 to +30 was amplified by PCR with primers PROHXT7-1 and PROHXT7-2 (see below), and plasmid p21-PST (Reifenberger et al., 1995, supra) as a template. The PCR product was cleaved with SpeI at both ends and cloned in the correct orientation into the SpeI site of plasmid pUG6 (Gueldener et al., 1996, supra) behind the second loxp site, resulting in plasmid pUG6-kPHXT7. This plasmid was then used as a template to generate by PCR with primers INTPH7-1 and INTPH7-2 a DNA molecule consisting of a kanMX-HXT7p marker cassette flanked by short homology sequences to the HXT3 promoter (−770 to −720) and HXT7 terminator regions. The 2.4 kb PCR product was transformed into strain EBY.VW4000 (whose HXT3-6-7 gene cluster is replaced by a loxP site), selecting for resistance to G418 (200 mg liter[−1]) on YPMaltose agar plates, and used to replace the HXT3 promoter-loxP region by the kanMX-HXT7p cassette. After transformation with plasmid pSH47, the kaMX marker was removed as described (Gueldener et al., 1996, supra), resulting in strain EBY.VW4002.

The HXT7 gene was amplified by PCR from plasmid p21-PST with primers C1-IHXT7 and C4-IHXT7. The PCR product containing short homology sequences to the HXT7 promoter-terminator expression cassette of strain EBY.VW4002 was transformed into this strain, selecting for growth on YPGlucose agar plates. Integration into the genomic expression cassette by homologous recombination resulted in strain JBY02 (HXT7+). To construct an FOA(5-fluoroorotic acid)-counterselectable marker-expression cassette in strain EBY.VW4002, the *K. lactis* URA3 ORF was PCR-amplified from strain MS7-62 (gift of C. Falcone, Rome) with primers I-KURA31 and I-KURA32 (see below), resulting in a DNA-fragment with the KlURA3 ORF flanked by short homology regions to the HXT7 promoter and HXT7 terminator. The DNA fragment was transformed into strain JBY02 selecting for growth on a synthetic medium without uracil and with maltose as the carbon source, resulting in strain EBY.VW4003 containing a genomically integrated HXT7 promoter$^{(-392-+1)}$-KlURA3-HXT7 terminator expression cassette. This strain was made prototropic (KOY.VW100) by transformation.

```
PROHXT7:                                   (SEQ ID NO: 14)
5'-GGACTAGTGA TATCTCTCGT AGGAACAATTTCGG-3'

PROHXT7-2:                                 (SEQ ID NO: 15)
5'-GGACTAGTTG CTCTGCAATAGCAGCGTC-3'

INTPH7-1:                                  (SEQ ID NO: 16)
5'-CCTATTCGTC ATCGCAGACA GCCTTCATCTTCTCGAGATA
ACACCTGGAG CGCGCGTTTC GGTGATGACG-3'

INTPH7-2:                                  (SEQ ID NO: 17)
5'-AAGTTTCTTT GTCTCCGTCC CACTCAACTTTCTGAGAACA
AATGATCCAT TTTTTGATTA AAATTAAAAA AAC-3'

C1-IHXT7:                                  (SEQ ID NO: 18)
5'-CCTGCGTGTT CTTCTGAGGTTC-3'

C4-IHXT7:                                  (SEQ ID NO: 19)
5'-TTTGTAGACG TGGGTCTGCAGGCA-3'

I-KURA31:                                  (SEQ ID NO: 20)
5'-CAAAGAATAA ACACAAAAAC AAAAAGTTTTTTTAATTTTA
ATCAAAAAAT GTCCACAAAA TCATATACCAGTAG-3'

I-KURA32:                                  (SEQ ID NO: 21)
5'-GCACAAATTA GAGCGTGATC ATGAATTAATAAAAGTGTTC
GCAAATTAAT GGGGAGCGCT GATTCTCTTT TG-3'
```

Integration of the different genes or constructs was done using homologous recombination. Recombinations were selected on YPGlucose (YPD 2% glucose) plates and then replica plated on to YNB 2% Maltose 5-FOA plates to select for out-recombination of URA3. To make the strains prototropic the URA3 was reintroduced by transformation and homologous recombination.

The chimeras or wild-type genes that have been integrated in the strain constitute the only hexose transporter.

The prototropic strains used in these experiments are wild type KOY.PK2-1C83, "null mutant" KOY.VW100, KOY.VWTM6P, KOY.VW101P and KOY.VW102P.

The strains used and generated are summarised in the following table:

TABLE 1

| Strain | Genotype | Source |
|---|---|---|
| KOY.PK2-1C83 | MATa MAL2-8c SUC2 | Auxotropic: K-D Entian (Van Dijken et al., 2000, Enzyme Microb. Technol., 26, p706-714 Prototropic: This study |
| KOY.VW100 | MATa MAL2-8c SUC2 hxt17ΔΔ 112ura3-52 gal2Δ::loxP stl1Δ::loxP agt1Δ::loxP ydl247wΔ::loxP yjr160cΔ::loxP hxt13Δ::loxP hxt15Δ::loxP hxt16Δ::loxP hxt14Δ::loxP hxt12Δ::loxP hxt9Δ::loxP hxt11Δ::loxP hxt10Δ::loxP hxt8Δ::loxP hxt514Δ::loxP hxt2Δ::loxP Hxt367Δ::loxP Integration cassette: (located at the former site of HXT367) strong constitutive promoter from HXT7 the *K. lactis* URA3 ORF for 5-FOA counter selection and HXT7 terminator. | Auxotropic: Eckhard Boles (Wieczorke et al., 1999, supra) and this study Prototropic: This study |
| KOY.TM4 | KOY.VW100 with TM4 construct integrated into cassette with subsequent out-recombination of *K. lactis* URA3 in the cassette. URA3 reintroduced to obtain a prototropic strain | This study |
| KOY.TM6P | KOY.VW100 with TM6 construct integrated into cassette with subsequent out-recombination of *K. lactis* URA3 in the cassette. URA3 reintroduced to obtain a prototropic strain | This study |
| KOY.VW101P | KOY.VW100 HXT1 construct integrated into cassette with subsequent out-recombination of *K. lactis* URA3 in the cassette. URA3 reintroduced to obtain a prototropic strain | This study |
| KOY.VW102P | KOY.VW100 HXT7 construct integrated into cassette with subsequent out-recombination of *K. lactis* URA3 in the cassette. URA3 reintroduced to obtain a prototropic strain | This study |

The protein sequence of TM6 is as follows (SEQ ID NO: 1):

```
MNSTPDLISP QKSNSSNSYE LESGRSKAMN TPEGKNESFH

DNLSESQVQP AVAPPNTGKG VYVTVSICCV MVAFGGFIFG

WDTGTISGFV AQTDFLRRFG MKHHDGSHYL SKVRTGLIVS

IFNIGCAIGG IVLAKLGDMY GRRIGLIVVV VIYTIGIIIQ

IASINKWYQY FIGRIISGLG VGGITVLSPM LISEVAPSEM

RGTLVSCYQV MITLGIFLGY CTNFGTKNYS NSVQWRVPLG
```

```
LCFAWALFMI  GGMTFVPESP  RYLAEVGKIE  EAKRSIAVYN

KVAVDDPSVL  AEVEAVLAGV  EAEKLAGNAS  WGELFSSKTK

VLQRLIMGAM  IQSLQQLTGD  NYFFYYGTTI  FKAVGLSDSF

ETSIVLGIVN  FASTFVGIYV  VERYGRRTCL  LWGAASMTAC

MVVYASVGVT  RLWPNGQDQP  SSKGAGNCMI  VFACFYIFCF

ATTWAPIPYV  VVSETFPLRV  KSKAMSIATA  ANWLWGFLIG

FFTPFITGAI  NFYYGYVFMG  CLVFMFFYVL  LVVPETKGLT

LEEVNTMWEE  GVLPWKSASW  VPPSRRGANY  DAEEMTHDDK

PLYKRMFSTK
```

At position 279 above, TM6 contains a tyrosine residues (shown in bold). This represents a modification relative to the naturally occurring sequence in HXT1 in which the residue is serine. As such, modification at this residue or comparable residues in other transporters forms a further preferred feature of the invention. However, sequences in which position 279 is a serine residue in the above sequence is also included within the scope of this invention.

The protein sequence of TM4 is as follows (SEQ ID NO: 2):

```
MNSTPDLISP  QKSNSSNSYE  LESGRSKAMN  TPEGKNESFH

DNLSESQVQP  AVAPPNTGKG  VYVTVSICCV  MVAFGGFIFG

WDTGTISGFV  AQTDFLRRFG  MKHHDGSHYL  SKVRTGLIVS

IFNIGCAIGG  IVLAKLGDMY  GRRIGLIVVV  VIYTIGIIIQ

IASINKWYQY  FIGRIISGLG  VGGIAVLSPM  LISEVSPKHL

RGTLVSCYQL  MITAGIFLGY  CTNFGTKNYS  NSVQWRVPLG

LCFAWALFMI  GGMTFVPESP  RYLAEVGKIE  EAKRSIAVSN

KVAVDDPSVL  AEVEAVLAGV  EAEKLAGNAS  WGELFSSKTK

VLQRLIMGAM  IQSLQQLTGD  NYFFYYGTTI  FKAVGLSDSF

ETSIVLGIVN  FASTFVGIYV  VERYGRRTCL  LWGAASMTAC

MVVYASVGVT  RLWPNGQDQP  SSKGAGNCMI  VFACFYIFCF

ATTWAPIPYV  VVSETFPLRV  KSKAMSIATA  ANWLWGFLIG

FFTPFITGAI  NFYYGYVFMG  CLVFMFFYVL  LVVPETKGLT

LEEVNTMWEE  GVLPWKSASW  VPPSRRGANY  DAEEMTHDDK

PLYKRMFSTK*
```

Functional constructs which have been identified are TM 1,2,3,4, 5, 6,10,11,12. These constructs, which form preferred aspects of the invention, are made using the following portion of HXT1: 1-231 (TM1), 1-391 (TM2), 1-449 (TM3), 1-551 (TM4), 1-627 (TM5), 1-741 (TM6), 1-1010 (TM7), 1-1108 (TM8), 1-1214 (TM9), 1-1293 (TM10), 1-1438 (TM11), 1-1504 (TM12), with the remainder made up of HXT7, e.g. 232-1713 in the case of TM1. No transformants for TM7,8,9 have yet been identified.

Saccharomyces cerevisiae KOY.TM6P has been deposited under the Budapest treaty on the 20$^{th}$ of Jun., 2000 at the Deutsche Sammiung von Mikroorganismen und Zellkulturen GmbH, Mascheroder Weg 1b. D-38124 Braunschweig, Germany under deposition number DSM 13555.

Saccharomyces cerevisiae KOY.TM4P has been deposited under the Budapest treaty on the 6 of Nov. 2000 at the Deutsche Sammlung Mikroorganismen under deposition number DSM 13832.

Growth Characterisation

Results

Figure 2:
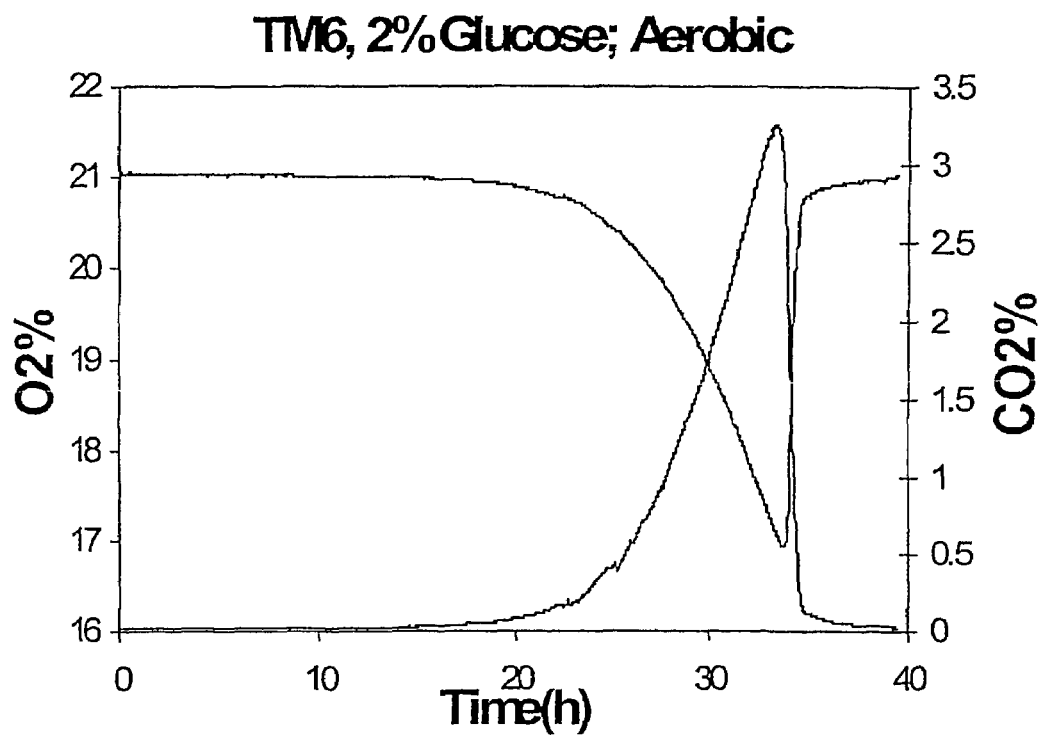
FIG. 2 shows oxygen consumption and carbon dioxide production under different phases of the growth cycle of S. cerevisiae of the prototropic TM6-expressing strain.
Figure 3:
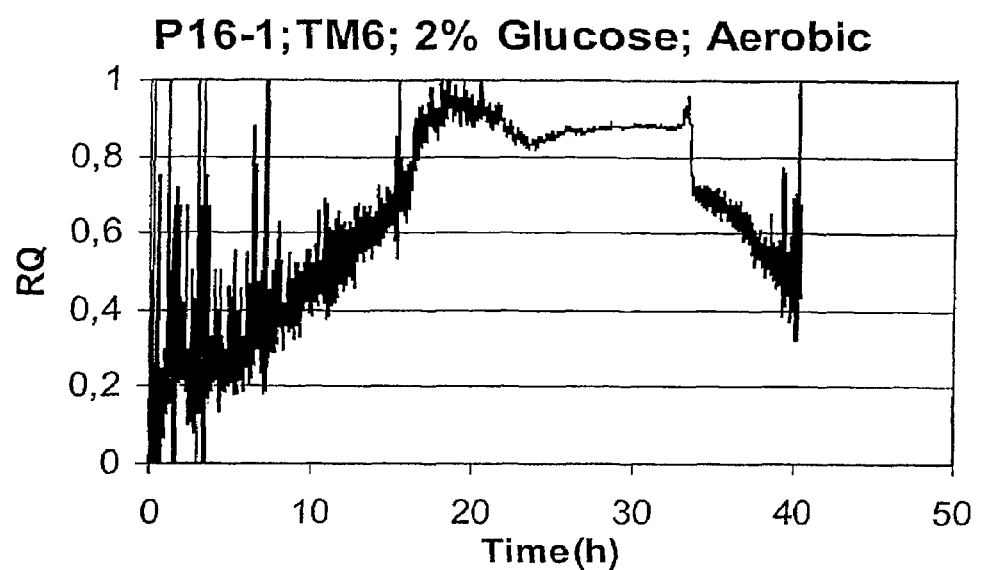
FIG. 3 shows a semilog-plot of the optical density versus time giving the measure of biomass growth during aerobic growth on glucose by the TM6-expressing strain.
Figure 4:
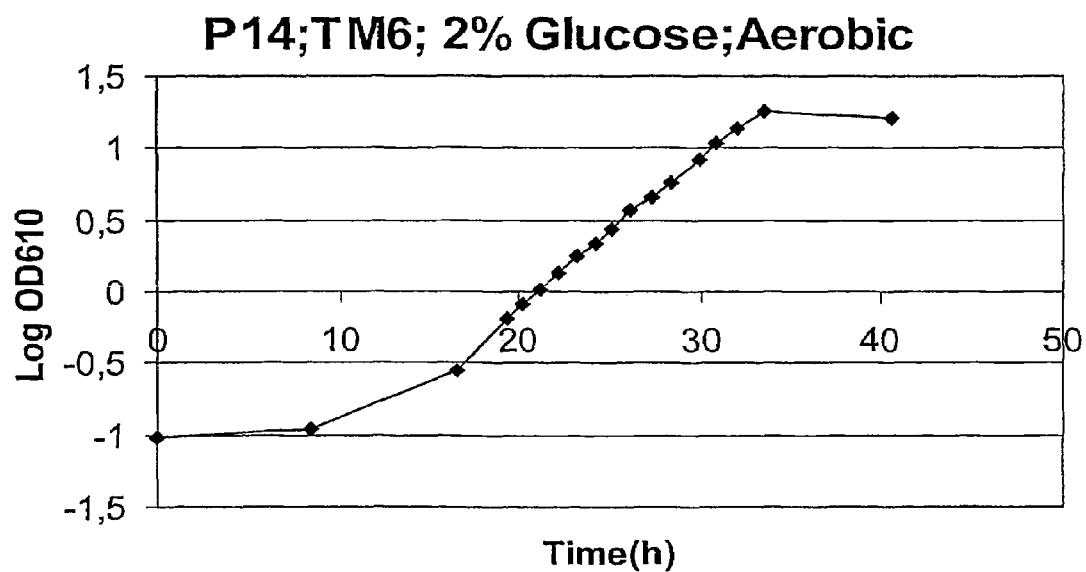
FIG. 4 shows a continuous on-line plot of the ratio between the carbon dioxide production rate and the oxygen consumption resulting in continuous monitoring of RQ during aerobic growth on glucose of the TM6-expressing strain. Measurements during the first 20 hrs should not be considered because of limiting sensitivity.
Figure 7A:
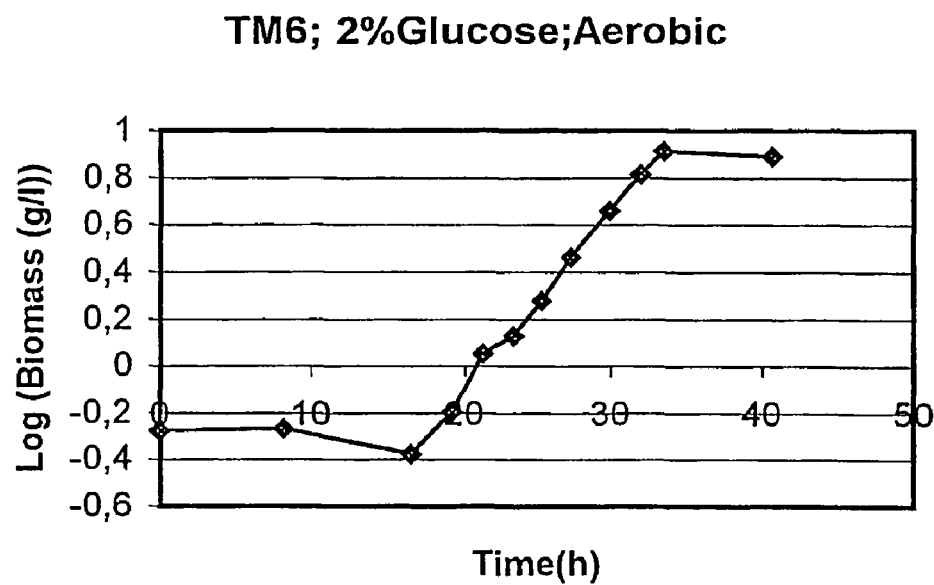
FIG. 7 shows a semilog-plot of the biomass(g/l)/time(h) for A) TM6 and B) TM4.
Figure 7B:
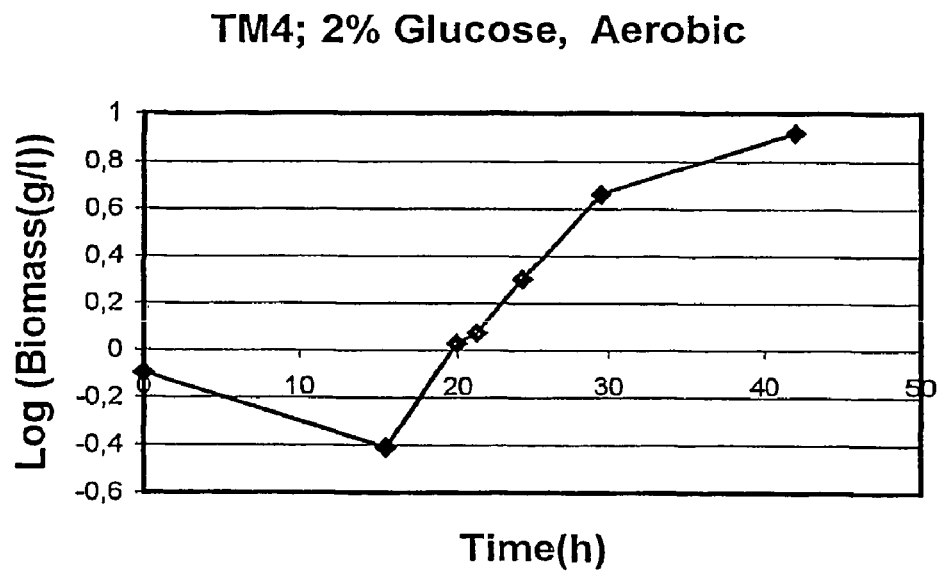

Aerobic growth: A diauxic growth behaviour typical for S. cerevisiae during aerobic batch cultivation on glucose is shown in FIG. 1 and was performed as described previously, ie. in the medium used by Verduyn et al. (1992, supra) at pH 5.00 in the presence of 5 mM glucose, with a starting culture of 0.3-0.7 g dry biomass in 1.51 fermentors, stirred at 1500 rpm and an air inflow of 0.5 volume of air per vessel volume per minute (vvm). The first phase observed in FIG. 1 is due to consumption of glucose with the concomitant production of ethanol and biomass. During the second phase, ethanol serves as the main carbon and energy source. However, during growth of KOY.TM6P a single growth phase is observed (FIG. 2). Apparently, the sugar is immediately converted to carbon dioxide and water without any formation of ethanol, i.e. de-repressed conditions are prevalent. During these conditions a generation time of 3.8 h was obtained. This may be calculated from FIG. 7 which shows the semi-log plot of biomass versus time. The maximal ethanol concentration was less than 0.12 g/l when using a glucose concentration of 20 g/l. Also other common by-products such as glycerol and acetate were found in negligible amounts. De-repressed conditions was also verified by the fact that on-line measurements of oxygen consumption rate and carbon dioxide formation rate revealed a respiratory quotient (RQ carbon dioxide formation rate/oxygen consumption rate) close to 1. FIG. 3.

Figure 5:
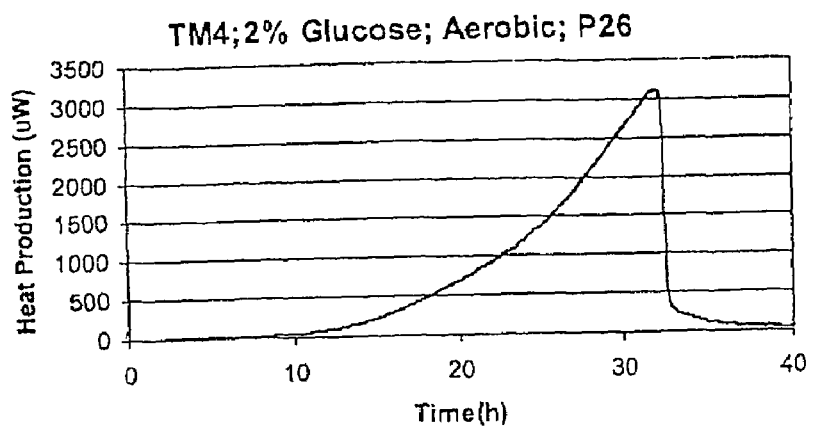
FIG. 5 shows on-line heat-production measurement for KOY.TM4P.
Figure 6:
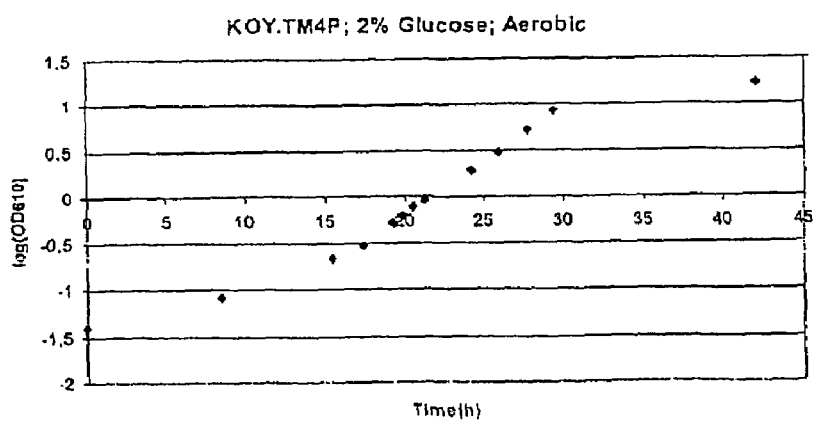
FIG. 6 shows a semilog-plot of the optical density versus time giving the measure of biomass growth on glucose by the TM4-expressing strain.

KOY.TM4P has also shown growth behaviour very similar to KOY.TM6P (FIG. 5). The generation time calculated from the semi-log plot of the optical density versus time has been shown to be 3 to 3.9 h (FIG. 6). The maximum ethanol production measured was 0.15 g/l when using 20 g/l of glucose in the medium. As with KOY.TM6P glycerol and ascetic acid were found at very low concentrations.

Anaerobic growth: The strain, KOY.TM6P, is able to produce ethanol during anaerobic conditions. It seems, however, that after an initial phase of fairly high activity (as indicated by the specific growth and ethanol production rates) an as yet unidentified factor becomes limiting. This factor can not be such as the essential sterol ergosterol, since supplements that are known to be needed were added to the culture.

Up-take Kinetics

Glucose uptake assays has been performed using radiolabelled glucose (Walsh et al., 1994, supra). Cells were grown in a defined medium containing 2% glucose. Cells were harvested at $OD_{610}$=1. Cells were washed and resuspended in 100 mM potassium phosphate buffer to a protein concentration of approximately 8-15 mg/ml. Cells were incubated with radiolabelled glucose for about 5 sec and the amount of intracellular glucose was determined by liquid scintillation counter.

The HXT1-expressing strain (expressing the most abundant low affinity transport protein) showed similar uptake kinetics as the low affinity uptake component in the wild type. Surprisingly, the HXT7-expressing strain, which expresses the most abundant high affinity protein, showed about the same growth behaviour as the wild type and the HXT1-expressing strain (data not shown). The only significant difference was that the latter had a much sharper transition during the diauxic phase when the culture shifts from respiro-fermentative to respiratory growth. In other words, the much lower $V_{max}$ of the uptake system in the HXT7 strain compared to that of the wild type and the HXT1 strain does not seem to restrict glucose consumption or the growth rate. It rather seems that the $K_m$ for uptake displayed by the strain is the factor determining a smooth metabolic shift from glucose to another carbon and energy source. However, even lower $V_{max}$ values, as obtained for the TM strains, seem to limit growth, resulting in diminished growth rates (data not shown).

Table 2. [Table 1.] Up-take kinetic data with glucose as substrate.

TABLE 2

Up-take kinetic data with glucose as substrate.

| Strain | $K_m$ (mM) | $V_{max}$ (nmol/min mg protein) |
|---|---|---|
| WT | 67 ± 14[b] | 818 ± 93[b] |
| (CEN.PK)[a] | 1.2 ± 1.2[b] | 80 ± 80[b] |
| HXT1 | 50-100 | 690 |
| HXT7 | 2-3 | 80 |
| TM1 | 2-3 | 35 |
| TM4 | 4-6 | 80 |
| TM6 | 7 | 38 |
| TM12 | 60 | 150 |

[a]Literature data (Diderich et al., 2000, in "Animating the cellular map", Stellenbosch University Press, South Africa, IBSN 0-7972-0776-7, p 271-275)
[b]The higher values refer to the low affinity uptake system and the lower values to the high affinity uptake system.

The results obtained for the various strains described in this Example may be summarized as follows:

TABLE 3

| | Wild-type | HXT1 | HXT7 | TM4 | TM6 |
|---|---|---|---|---|---|
| Generation time (h) | 2 | 2.5 | 2.7 | 3-3.9 | 3.8 |
| Growth yield (biomass/g glucose) | 0.3-0.5 | 0.3-0.35 | 0.33-0.38 | 0.34-0.37 | 0.41 |
| Glucose consumption (mmol glucose/(g biomass · h)) | 10 | 10 | <10 | 2.5 | 3-4 |
| $O_2$ consumption rate (mmol $O_2$/(g biomass · h)) | 2-2.5 | 3-4 | 2.2-6.1* | n.d. | 3-4.5 |
| ethanol production (g/l) | 7 | 6.2 | 5.2 | 0.15 | 0.12 |

*Reflects continuous increase during the batch culture.
n.d.: not determined

```
Sequence listing No. 1 (SEQ ID NO: 1):
Hexose transporter region of Saccharomyces
cerevisiae KOY.TM6P bp 1-741 of HXTI and bp
742-1713 of HXT7.
MNSTPDLISP QKSNSSNSYE LESGRSKAMN TPEGKNESFH

DNLSESQVQP AVAPPNTGKG VYVTVSICCV MVAFGGFIFG

WDTGTISGFV AQTDFLRRFG MKHHDGSHYL SKVRTGLIVS

IFNIGCAIGG IVLAKLGDMY GRRIGLIVVV VIYTIGIIIQ

IASINKWYQY FIGRIISGLG VGGITVLSPM LISEVAPSEM

RGTLVSCYQV MITLGIFLGY CTNFGTKNYS NSVQWRVPLG

LCFAWALFMI GGMTFVPESP RYLAEVGKIE EAKRSIAVYN

KVAVDDPSVL AEVEAVLAGV EAEKLAGNAS WGELFSSKTK

VLQRLIMGAM IQSLQQLTGD NYFFYYGTTI FKAVGLSDSF

ETSIVLGIVN FASTFVGIYV VERYGRRTCL LWGAASMTAC

MVVYASVGVT RLWPNGQDQP SSKGAGNCMI VFACFYIFCF

ATTWAPIPYV VVSETFPLRV KSKAMSIATA ANWLWGFLIG

FFTPFITGAI NFYYGYVFMG CLVFMFFYVL LVVPETKGLT

LEEVNTMWEE GVLPWKSASW VPPSRRGANY DAEEMTHDDK

PLYKRMFSTK

Sequence listing No. 2 (SEQ ID NO: 2):
Hexose transporter region of Saccharomyces
cerevisiae KOY.TM4P bp 1-551 of HXT1 and bp
552-1713 of HXT7.
MNSTPDLISP QKSNSSNSYE LESGRSKAMN TPEGKNESFH

DNLSESQVQP AVAPPNTGKG VYVTVSICCV MVAFGGFIFG

WDTGTISGFV AQTDFLRRFG MKHHDGSHYL SKVRTGLIVS

IFNIGCAIGG IVLAKLGDMY GRRIGLIVVV VIYTIGIIIQ

IASINKWYQY FIGRIISGLG VGGIAVLSPM LISEVSPKHL

RGTLVSCYQL MITAGIFLGY CTNFGTKNYS NSVQWRVPLG

LCFAWALFMI GGMTFVPESP RYLAEVGKIE EAKRSIAVSN

KVAVDDPSVL AEVEAVLAGV EAEKLAGNAS WGELFSSKTK

VLQRLIMGAM IQSLQQLTGD NYFFYYGTTI FKAVGLSDSF

ETSIVLGIVN FASTFVGIYV VERYGRRTCL LWGAASMTAC

MVVYASVGVT RLWPNGQDQP SSKGAGNCMI VFACFYIFCF

ATTWAPIPYV VVSETFPLRV KSKAMSIATA ANWLWGFLIG

FFTPFITGAI NFYYGYVFMG CLVFMFFYVL LVVPETKGLT

LEEVNTMWEE GVLPWKSASW VPPSRRGANY DAEEMTHDDK

PLYKRMFSTK*

(SEQ ID NO: 3) TM4 - nucleotide sequence
atgaattcaa ctcccgatct aatatctcct cagaaatcca attcatccaa ctcatatgaa ttggaatctg gtcgttcaaa ggccatgaat actccagaag gtaaaaatga aagttttcac gacaacttaa gtgaaagtca agtgcaaccc gccgttgccc ctccaaacac cggaaaaggt gtctacgtaa cggtttctat ctgttgtgtt atggttgctt tcggtggttt catatttgga tgggatactg gtaccatttc tggttttgtt gctcaaactg attttctaag aagatttggt atgaagcacc acgacggtag tcattacttg tccaaggtga gaactggttt aattgtctct attttttaaca ttggttgtgc cattggtggt atcgtcttag ccaagctagg tgatatgtat ggtcgtagaa tcggtttgat tgtcgttgta gtaatctaca ctatcggtat cattattcaa atagcctcga tcaacaagtg gtaccaatat ttcattggta gaattatctc tggtttaggt gtcggtggta ttgccgtttt
```

-continued atctcctatg ttgatttctg aagtatcccc aaagcattta
aggggtactt tagtctcttg ctaccaattg atgattactg
ccggtatttt cttgggttac tgtaccaact tcggtactaa
gaactactcc aactctgtgc aatggagagt tccattaggt
ttgtgttttg cctgggcttt gtttatgatt ggtggtatga
catttgttcc agagtctcca cgttatttgg ctgaagtcgg
taagatcgaa gaagccaaac gttctattgc cgtttctaac
aaggttgctg ttgatgatcc atctgttttg gctgaagtcg
aagctgtctt ggctggtgta gaggcagaga aattagctgg
taatgcatcc tggggtgaat gtttagtag caagacaaag
gtccttcagc gtttgatcat gggtgctatg attcaatctc
tacaacaatt gacaggtgat aactatttct tctactatgg
tactactatt ttcaaggctg ttggtttgag tgactctttc
gaaacctcta ttgtcttggg tattgttaac tttgcttcca
cctttgttgg tatttacgtt gttgagagat atggtcgtcg
tacttgtttg ctatggggtg ctgcatccat gactgcttgt
atggttgtct atgcttccgt gggtgtcacc agattatggc
caaatggtca agaccaacca tcttccaagg gtgctggtaa
ctgtatgatt gtctttgcct gtttctatat tttctgtttt
gctactacat gggctccaat tccttatgtc gttgtttctg
aaactttccc attgagagtc aagtctaagg ctatgtctat
tgctacagct gctaattggt tgtggggttt cttgattggt
ttcttcactc catttattac tggtgctatt aacttctact
acggttacgt tttcatgggc tgtttggtct tcatgttctt
ctatgttttg ttagttgttc cagaaactaa gggtttgact
ttggaagaag tcaacaccat gtgggaagaa ggtgttctac
catggaagtc tgcctcatgg gttccaccat ccagaagagg
tgccaactac gacgctgaag aaatgactca cgatgacaag
ccattgtaca agagaatgtt cagcaccaaa taa
(SEQ ID NO: 4): TM6 - nucleotide sequence
atgaattcaa ctcccgatct aatatctcct cagaaatcca
attcatccaa ctcatatgaa ttggaatctg tcgttcaaa
ggccatgaat actccagaag gtaaaaatga agttttcac
gacaacttaa gtgaaagtca agtgcaaccc gccgttgccc
ctccaaacac cggaaaaggt gtctacgtaa cggtttctat
ctgttgtgtt atggttgctt tcggtggttt catatttgga
tgggatactg gtaccatttc tggttttgtt gctcaaactg
attttctaag aagatttggt atgaagcacc acgacggtag
tcattacttg tccaaggtga gaactggttt aattgtctct
attttttaaca ttggttgtgc cattggtggt atcgtcttag
ccaagctagg tgatatgtat ggtcgtagaa tcggtttgat -continued tgtcgttgta gtaatctaca ctatcggtat cattattcaa
atagcctcga tcaacaagtg gtaccaatat ttcattggta
gaattatctc tggtttaggt gtcggtggta tcacagtttt
atctcccatg ctaatatctg aggtcgcccc cagtgaaatg
agaggcacct tggtttcatg ttaccaagtc atgattactt
taggtatttt cttaggttac tgtaccaatt ttggtaccaa
gaattactca aactctgtcc aatggagagt tccattaggt
ttgtgtttcg cctgggcctt atttatgatt ggtggtatga
catttgttcc agagtctcca cgttatttgg ctgaagtcgg
taagatcgaa gaagccaaac gttctattgc cgtttataac
aaggttgctg ttgatgatcc atctgttttg gctgaagtcg
aagctgtctt ggctggtgta gaggcagaga aattagctgg
taatgcatcc tggggtgaat gtttagtag caagacaaag
gtccttcagc gtttgatcat gggtgctatg attcaatctc
tacaacaatt gacaggtgat aactatttct tctactatgg
tactactatt ttcaaggctg ttggtttgag tgactctttc
gaaacctcta ttgtcttggg tattgttaac tttgcttcca
cctttgttgg tatttacgtt gttgagagat atggtcgtcg
tacttgtttg ctatggggtg ctgcatccat gactgcttgt
atggttgtct atgcttccgt gggtgtcacc agattatggc
caaatggtca agaccaacca tcttccaagg gtgctggtaa
ctgtatgatt gtctttgcct gtttctatat tttctgtttt
gctactacat gggctccaat tccttatgtc gttgtttctg
aaactttccc attgagagtc aagtctaagg ctatgtctat
tgctacagct gctaattggt tgtggggttt cttgattggt
ttcttcactc catttattac tggtgctatt aacttctact
acggttacgt tttcatgggc tgtttggtct tcatgttctt
ctatgttttg ttagttgttc cagaaactaa gggtttgact
ttggaagaag tcaacaccat gtgggaagaa ggtgttctac
catggaagtc tgcctcatgg gttccaccat ccagaagagg
tgccaactac gacgctgaag aaatgactca cgatgacaag
ccattgtaca agagaatgtt cagcaccaaa taa
(SEQ ID NO: 5) Expression cassette
sequence - nucleotide sequence
tctcgtagga acaatttcgg gcccctgcgt gttcttctga
ggttcatctt ttacatttgc ttctgctgga taattttcag
aggcaacaag gaaaaattag atggcaaaaa gtcgtctttc
aaggaaaaat ccccaccatc tttcgagatc ccctgtaact
tattggcaac tgaaagaatg aaaaggagga aaatacaaaa
tatactagaa ctgaaaaaaa aaagtataa atagagacga
tatatgccaa tacttcacaa tgttcgaatc tattcttcat

```
ttgcagctat tgtaaaataa taaaacatca agaacaaaca
agctcaactt gtctttctta agaacaaaga ataaacacaa
aaacaaaaag tttttttaat tttaatcaaa aaatgtccac
aaaatcatat accagtagag ctgagactca tgcaagtccg
gttgcatcga aacttttacg tttaatggat gaaaagaaga
ccaatttgtg tgcttctctt gacgttcgtt cgactgatga
gctattgaaa cttgttgaaa cgttgggtcc atacatttgc
cttttgaaaa cacacgttga tatcttggat gatttcagtt
atgagggtac tgtcgttcca ttgaaagcat ggcagagaa
atacaagttc ttgatatttg aggacagaaa attcgccgat
atcggtaaca cagtcaaatt acaatataca tcgggcgttt
accgtatcgc agaatggtct gatatcacca acgcccacgg
ggttactggt gctggtattg ttgctggctt gaaacaaggt
gcgcaagagg tcaccaaaga accaagggga ttattgatgc
ttgctgaatt gtcttccaag ggttctctag cacacggtga
atatactaag ggtaccgttg atattgcaaa gagtgataaa
gatttcgtta ttgggttcat tgctcagaac gatatgggag
gaagagaaga agggtttgat tggctaatca tgaccccagg
```

```
tgtaggttta gacgacaaag gcgatgcatt gggtcagcag
tacagaaccg tcgacgaagt tgtaagtggt ggatcagata
tcatcattgt tggcagagga ctttttcgcca agggtagaga
tcctaaggtt gaaggtgaaa gatacagaaa tgctggatgg
gaagcgtacc aaaagagaat cagcgctccc cattaattg
cgaacacttt tattaattca tgatcacgct ctaatttgtg
catttgaaat gtactctaat tctaatttta tatttttaat
gatatcttga aaagtaaata cgttttttaat atatacaaaa
taatacagtt taattttcaa gttttttgatc atttgttctc
agaaagttga gtgggacgga gacaaagaaa ctttaaagag
aaatgcaaag tgggaagaag tcagttgttt accgaccgca
ctgttattca caaatattcc aattttgcct gcagaccac
gtctacaaat tttggttagt ttggtaaatg gtaaggatat
agtagagcct ttttgaaatg ggaaatatct tcttttttctg
tatcccgctt caaaaagtgt ctaatgagtc agttatttct
ttcttactca tcgcccgtca cttaaaagaa gaaaaattac
tttcatgatg cgaagcgaaa aaaatttta gcttcaattt
tcacaatgca tct
```

The invention claimed is:

1. A modified *Saccharomyces cerevisiae* yeast which produces lower levels of ethanol than wild-type yeast under aerobic conditions and glucose concentrations of 2%, and which exhibits a growth rate of at least 30% of the wild-type yeast, wherein said yeast contains a chimeric nucleotide sequence (a chimeric construct) which is stably transformed into the genetic material of the yeast, wherein the construct comprises a sequence having the form

A-B wherein

A is a first sequence comprising nucleotide bases w to x;

B is a second sequence comprising nucleotide bases (x+y) to z; wherein

A is from a nucleotide sequence encoding a *Saccharomyces cerevisiae* glucose transporter selected from HXT-1 (SEQ ID NO:22) or HXT-3 (SEQ ID NO:24) or encoding a sequence which exhibits at least 80% sequence identity to HXT1 (SEQ ID NO:22) or HXT-3 (SEQ ID NO:24), or the sequence complementary to any of the aforesaid sequences and B is from a nucleotide sequence encoding a *Saccharomyces cerevisiae* glucose transporter selected from HXT-2 (SEQ ID NO:23), HXT-4 (SEQ ID NO:25), HXT-6 (SEQ ID NO:26), HXT-7 (SEQ ID NO:27) or GAL2 (SEQ ID NO:28) or encoding a sequence which exhibits at least 80% sequence identity to HXT-2, HXT-4, HXT-6, HXT-7 or GAL-2, or the sequence complementary to any of the aforesaid sequences;

w is a first position within the nucleotide sequence from which said first sequence is derived, and is from 1 to 10;

x is a second position within the nucleotide sequence from which said first sequence is derived and is from 400 to 900;

y is an integer less than 3;

x+y is a first position within the nucleotide sequence from which said second sequence is derived;

and z is a second position within the nucleotide sequence from which said second sequence is derived and is greater than x+y and is from 1600 to 1713;

wherein said values refer to the position within the nucleotide sequence of said glucose transporter, and wherein said chimeric nucleotide sequence is introduced into a yeast cell which is a null strain which exhibits a glucose uptake of less than 2 nmol glucose/min/mg biomass to provide said modified *Saccharomyces cerevisiae* yeast.

2. A yeast as claimed in claim 1 wherein said yeast produces less than 0.6 g/l ethanol.

3. A yeast as claimed in claim 1 wherein said yeast produces less than 0.25 g/l ethanol.

4. A yeast as claimed in claim 1 wherein said yeast produces less than 50% ethanol compared to the wild-type yeast.

5. A yeast as claimed in claim 1 wherein said yeast exhibits a growth rate of at least 50% of the wild-type yeast.

6. A yeast as claimed in claim 1 wherein said construct comprises sequences from
   (i) the sequence encoding HXT-1 SEQ ID NO:22 or a sequence which exhibits at least 80% sequence identity to said HXT-1 sequence or the sequence complementary to any of the aforesaid sequences and
   (ii) the sequence encoding HXT-7 (SEQ ID NO:27) or a sequence which exhibits at least 80% sequence identity to said HXT-7 sequence or the sequence complementary to any of the aforesaid sequences.

7. A yeast as claimed in claim 1 wherein x=551 or 741, w and y=1 and z=1713.

8. A yeast as claimed in claim 1 wherein said chimeric construct encodes a chimeric polypeptide having a total of 10 to 14 transmembrane domains.

9. A yeast as claimed in claim 1 wherein said construct comprises:

nucleotides 1-449 from the nucleotide sequence encoding HXT-1 (SEQ ID NO: 22) and nucleotides 450-1713 from the nucleotide sequence encoding HXT-7 (SEQ ID NO: 27);

nucleotides 1-551 from the nucleotide sequence encoding HXT-1 (SEQ ID NO: 22) and nucleotides 552-1713 from the nucleotide sequence encoding HXT-7 SEQ ID NO:27);

nucleotides 1-627 from the nucleotide sequence encoding HXT-1 (SEQ ID NO: 22) and nucleotides 628-1713 from the nucleotide sequence encoding HXT-7 (SEQ ID NO:27);

or a nucleic acid molecule which exhibits at least 80% sequence identity to said construct or the sequence complementary to any of the aforementioned sequences or constructs.

10. A yeast as claimed in claim 1 wherein the yeast cell into which said chimeric construct is introduced is a null strain without saccharide transporting properties.

11. A yeast as claimed in claim 1 wherein said chimeric construct comprises (i) the nucleotide sequence encoding SEQ ID NO: 1 or 2 or the nucleotide sequence of SEQ ID NO: 3 or 4, (ii) a sequence which exhibits at least 80% sequence identity to one of said sequences in (i), or (iii) the sequence complementary to any of the aforesaid sequences.

12. A yeast as claimed in claim 11 denoted *Saccharomyces cerevisiae* KOY.TM4P or KOY.TM6P having the deposition number DSM (Deutsche Sammlung Mikroorganismen) 13832 or DSM 13555, respectively.

13. A nucleic acid molecule comprising a chimeric nucleotide sequence as defined in claim 1 wherein B is from a nucleotide sequence encoding a *Saccharomyces cerevisiae* glucose transporter selected from HXT-2 (SEQ ID NO:23), HXT-4 (SEQ ID NO:25), HXT-6 (SEQ ID NO:26), or HXT-7 (SEQ ID NO: 27), or encoding a sequence which exhibits at least 80% sequence identity to HXT-2, HXT-4, HXT-6 or HXT-7, or the sequence complementary thereto.

14. A vector or host cell comprising a nucleic acid molecule as defined in claim 13.

15. A polypeptide comprising a sequence encoded by a nucleic acid molecule as defined in claim 13.

16. A method of inserting exogenous genetic material into a yeast cell as defined in claim 1 to provide a yeast cell which produces a product, said method comprising at least the steps of introducing said material into said cell, wherein said exogenous material encodes said product or portion thereof or encodes a polypeptide or part thereof which facilitates the direct or indirect production of said product or portion thereof, or which affects the expression of said polypeptide or product.

17. A method as claimed in claim 16 wherein said product is a metabolite, a chemical, a food stuff or a therapeutic agent.

18. A method as claimed in claim 16 wherein said product is an amino acid, a peptide, a polypeptide, a sugar, a small polyol or $CO_2$.

19. A yeast cell obtainable by the method of claim 16, 17, or 18.

20. A method of preparing a product, comprising growing yeast cells as defined in claim 1 under aerobic conditions in the presence of 2% saccharide concentrations.

21. A method as claimed in claim 20, additionally comprising the step of isolating the product thus formed.

22. A method as claimed in claim 20 or 21 wherein said product is a low alcohol beer with less than 1% alcohol w/v, a low alcohol wine with less than 10% alcohol w/v or a non-alcoholic beverage.

23. A yeast as claimed in claim 5, wherein said yeast exhibits a growth rate of at least 70% of the wild-type yeast.

* * * * *

SEQUENCE LISTING

<160> NUMBER OF SEQ ID NOS: 28

<210> SEQ ID NO 1
<211> LENGTH: 570
<212> TYPE: PRT
<213> ORGANISM: Artificial Sequence
<220> FEATURE:
<223> OTHER INFORMATION: amino acid chimera derived from S. cerevisiae sequences

<400> SEQUENCE: 1

Met Asn Ser Thr Pro Asp Leu Ile Ser Pro Gln Lys Ser Asn Ser Ser
1               5                   10                  15

Asn Ser Tyr Glu Leu Glu Ser Gly Arg Ser Lys Ala Met Asn Thr Pro
            20                  25                  30

Glu Gly Lys Asn Glu Ser Phe His Asp Asn Leu Ser Glu Ser Gln Val
        35                  40                  45

Gln Pro Ala Val Ala Pro Pro Asn Thr Gly Lys Gly Val Tyr Val Thr
    50                  55                  60

Val Ser Ile Cys Cys Val Met Val Ala Phe Gly Gly Phe Ile Phe Gly
65                  70                  75                  80

Trp Asp Thr Gly Thr Ile Ser Gly Phe Val Ala Gln Thr Asp Phe Leu
                85                  90                  95

Arg Arg Phe Gly Met Lys His His Asp Gly Ser His Tyr Leu Ser Lys
            100                 105                 110

Val Arg Thr Gly Leu Ile Val Ser Ile Phe Asn Ile Gly Cys Ala Ile
        115                 120                 125

```
Gly Gly Ile Val Leu Ala Lys Leu Gly Asp Met Tyr Gly Arg Arg Ile
            130                 135                 140

Gly Leu Ile Val Val Val Ile Tyr Thr Ile Gly Ile Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Thr Val Leu Ser Pro Met Leu Ile
                180                 185                 190

Ser Glu Val Ala Pro Ser Glu Met Arg Gly Thr Leu Val Ser Cys Tyr
                195                 200                 205

Gln Val Met Ile Thr Leu Gly Ile Phe Leu Gly Tyr Cys Thr Asn Phe
            210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
                260                 265                 270

Lys Arg Ser Ile Ala Val Tyr Asn Lys Val Ala Val Asp Asp Pro Ser
                275                 280                 285

Val Leu Ala Glu Val Glu Ala Val Leu Ala Gly Val Glu Ala Glu Lys
            290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
                325                 330                 335

Leu Thr Gly Asp Asn Tyr Phe Phe Tyr Tyr Gly Thr Thr Ile Phe Lys
                340                 345                 350

Ala Val Gly Leu Ser Asp Ser Phe Glu Thr Ser Ile Val Leu Gly Ile
                355                 360                 365

Val Asn Phe Ala Ser Thr Phe Val Gly Ile Tyr Val Val Glu Arg Tyr
            370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
                405                 410                 415

Gln Asp Gln Pro Ser Ser Lys Gly Ala Gly Asn Cys Met Ile Val Phe
                420                 425                 430

Ala Cys Phe Tyr Ile Phe Cys Phe Ala Thr Thr Trp Ala Pro Ile Pro
            435                 440                 445

Tyr Val Val Ser Glu Thr Phe Pro Leu Arg Val Lys Ser Lys Ala
                450                 455                 460

Met Ser Ile Ala Thr Ala Ala Asn Trp Leu Trp Gly Phe Leu Ile Gly
465                 470                 475                 480

Phe Phe Thr Pro Phe Ile Thr Gly Ala Ile Asn Phe Tyr Tyr Gly Tyr
                485                 490                 495

Val Phe Met Gly Cys Leu Val Phe Met Phe Phe Tyr Val Leu Leu Val
                500                 505                 510

Val Pro Glu Thr Lys Gly Leu Thr Leu Glu Glu Val Asn Thr Met Trp
            515                 520                 525

Glu Glu Gly Val Leu Pro Trp Lys Ser Ala Ser Trp Val Pro Pro Ser
530                 535                 540
```

Arg Arg Gly Ala Asn Tyr Asp Ala Glu Glu Met Thr His Asp Asp Lys
545                 550                 555                 560

Pro Leu Tyr Lys Arg Met Phe Ser Thr Lys
                565                 570

<210> SEQ ID NO 2
<211> LENGTH: 570
<212> TYPE: PRT
<213> ORGANISM: Artificial Sequence
<220> FEATURE:
<223> OTHER INFORMATION: amino acid chimera derived from S. cerevisiae
      sequences

<400> SEQUENCE: 2

Met Asn Ser Thr Pro Asp Leu Ile Ser Pro Gln Lys Ser Asn Ser Ser
1               5                   10                  15

Asn Ser Tyr Glu Leu Glu Ser Gly Arg Ser Lys Ala Met Asn Thr Pro
                20                  25                  30

Glu Gly Lys Asn Glu Ser Phe His Asp Asn Leu Ser Glu Ser Gln Val
            35                  40                  45

Gln Pro Ala Val Ala Pro Pro Asn Thr Gly Lys Gly Val Tyr Val Thr
50                  55                  60

Val Ser Ile Cys Cys Val Met Val Ala Phe Gly Gly Phe Ile Phe Gly
65                  70                  75                  80

Trp Asp Thr Gly Thr Ile Ser Gly Phe Val Ala Gln Thr Asp Phe Leu
                85                  90                  95

Arg Arg Phe Gly Met Lys His His Asp Gly Ser His Tyr Leu Ser Lys
            100                 105                 110

Val Arg Thr Gly Leu Ile Val Ser Ile Phe Asn Ile Gly Cys Ala Ile
        115                 120                 125

Gly Gly Ile Val Leu Ala Lys Leu Gly Asp Met Tyr Gly Arg Arg Ile
130                 135                 140

Gly Leu Ile Val Val Val Val Ile Tyr Thr Ile Gly Ile Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Ala Val Leu Ser Pro Met Leu Ile
            180                 185                 190

Ser Glu Val Ser Pro Lys His Leu Arg Gly Thr Leu Val Ser Cys Tyr
        195                 200                 205

Gln Leu Met Ile Thr Ala Gly Ile Phe Leu Gly Tyr Cys Thr Asn Phe
210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
            260                 265                 270

Lys Arg Ser Ile Ala Val Ser Asn Lys Val Ala Val Asp Asp Pro Ser
        275                 280                 285

Val Leu Ala Glu Val Glu Ala Val Leu Ala Gly Val Glu Ala Glu Lys
290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
                325                 330                 335

Leu Thr Gly Asp Asn Tyr Phe Phe Tyr Tyr Gly Thr Thr Ile Phe Lys
            340                 345                 350

Ala Val Gly Leu Ser Asp Ser Phe Glu Thr Ser Ile Val Leu Gly Ile
        355                 360                 365

Val Asn Phe Ala Ser Thr Phe Val Gly Ile Tyr Val Val Glu Arg Tyr
    370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
        405                 410                 415

Gln Asp Gln Pro Ser Ser Lys Gly Ala Gly Asn Cys Met Ile Val Phe
            420                 425                 430

Ala Cys Phe Tyr Ile Phe Cys Phe Ala Thr Thr Trp Ala Pro Ile Pro
            435                 440                 445

Tyr Val Val Val Ser Glu Thr Phe Pro Leu Arg Val Lys Ser Lys Ala
        450                 455                 460

Met Ser Ile Ala Thr Ala Ala Asn Trp Leu Trp Gly Phe Leu Ile Gly
465                 470                 475                 480

Phe Phe Thr Pro Phe Ile Thr Gly Ala Ile Asn Phe Tyr Tyr Gly Tyr
                485                 490                 495

Val Phe Met Gly Cys Leu Val Phe Met Phe Phe Tyr Val Leu Leu Val
            500                 505                 510

Val Pro Glu Thr Lys Gly Leu Thr Leu Glu Glu Val Asn Thr Met Trp
        515                 520                 525

Glu Glu Gly Val Leu Pro Trp Lys Ser Ala Ser Trp Val Pro Pro Ser
530                 535                 540

Arg Arg Gly Ala Asn Tyr Asp Ala Glu Glu Met Thr His Asp Asp Lys
545                 550                 555                 560

Pro Leu Tyr Lys Arg Met Phe Ser Thr Lys
            565                 570

<210> SEQ ID NO 3
<211> LENGTH: 1713
<212> TYPE: DNA
<213> ORGANISM: Artificial Sequence
<220> FEATURE:
<223> OTHER INFORMATION: nucleic acid chimera derived from S. cerevisiae
      sequences

<400> SEQUENCE: 3
atgaattcaa ctcccgatct aatatctcct cagaaatcca attcatccaa ctcatatgaa     60
ttggaatctg tcgttcaaa ggccatgaat actccagaag gtaaaaatga agttttcac     120 gacaacttaa gtgaaagtca agtgcaaccc gccgttgccc ctccaaacac cggaaaaggt    180
gtctacgtaa cggtttctat ctgttgtgtt atggttgctt cggtggtttt catatttgga    240
tgggatactg gtaccatttc tggttttgtt gctcaaactg attttctaag aagatttggt    300
atgaagcacc acgacggtag tcattacttg tccaaggtga aactggtttt aattgtctct    360
atttttaaca ttggttgtgc cattggtggt atcgtcttag ccaagctagg tgatatgtat    420
ggtcgtagaa tcggtttgat tgtcgttgta gtaatctaca ctatcggtat cattattcaa    480
atagcctcga tcaacaagtg gtaccaatat ttcattggta gaattatctc tggtttaggt    540
gtcggtggta ttgccgtttt atctcctatg ttgattctg aagtatcccc aaagcattta    600 agggggtactt tagtctcttg ctaccaattg atgattactg ccggtatttt cttgggttac    660

-continued

```
tgtaccaact tcggtactaa gaactactcc aactctgtgc aatggagagt tccattaggt      720
ttgtgttttg cctgggcttt gtttatgatt ggtggtatga catttgttcc agagtctcca      780
cgttatttgg ctgaagtcgg taagatcgaa gaagccaaac gttctattgc cgtttctaac      840
aaggttgctg ttgatgatcc atctgttttg gctgaagtcg aagctgtctt ggctggtgta      900
gaggcagaga aattagctgg taatgcatcc tggggtgaat tgtttagtag caagacaaag      960
gtccttcagc gtttgatcat gggtgctatg attcaatctc tacaacaatt gacaggtgat     1020
aactatttct tctactatgg tactactatt ttcaaggctg ttggtttgag tgactctttc     1080
gaaacctcta ttgtcttggg tattgttaac tttgcttcca cctttgttgg tatttacgtt     1140
gttgagagat atggtcgtcg tacttgtttg ctatggggtg ctgcatccat gactgcttgt     1200
atggttgtct atgcttccgt gggtgtcacc agattatggc aaatggtca agaccaacca      1260
tcttccaagg gtgctggtaa ctgtatgatt gtctttgcct gtttctatat tttctgtttt     1320
gctactacat gggctccaat tcctatgtc gttgtttctg aaactttccc attgagagtc      1380
aagtctaagg ctatgtctat tgctacagct gctaattggt tgtggggttt cttgattggt     1440
ttcttcactc catttattac tggtgctatt aacttctact acggttacgt tttcatgggc     1500
tgtttggtct tcatgttctt ctatgttttg ttagttgttc cagaaactaa gggtttgact     1560
ttggaagaag tcaacaccat gtgggaagaa ggtgttctac catggaagtc tgcctcatgg     1620
gttccaccat ccagaagagg tgccaactac gacgctgaag aaatgactca cgatgacaag     1680
ccattgtaca agagaatgtt cagcaccaaa taa                                  1713
```

<210> SEQ ID NO 4
<211> LENGTH: 1713
<212> TYPE: DNA
<213> ORGANISM: Artificial Sequence
<220> FEATURE:
<223> OTHER INFORMATION: nucleic acid chimera derived from S. cerevisiae
      sequences

<400> SEQUENCE: 4

```
atgaattcaa ctcccgatct aatatctcct cagaaatcca attcatccaa ctcatatgaa       60
ttggaatctg gtcgttcaaa ggccatgaat actccagaag gtaaaaatga agttttcac       120
gacaacttaa gtgaaagtca agtgcaaccc gccgttgccc ctccaaacac cggaaaaggt      180
gtctacgtaa cggtttctat ctgttgtgtt atggttgctt tcggtggttt catatttgga      240
tgggatactg gtaccatttc tggttttgtt gctcaaactg atttttctaag aagatttggt      300
atgaagcacc acgacggtag tcattacttg tccaaggtga aactggtttt aattgtctct     360
attttttaaca ttggttgtgc cattggtggt atcgtcttag ccaagctagg tgatatgtat     420
ggtcgtagaa tcggtttgat tgtcgttgta gtaatctaca ctatcggtat cattattcaa      480
atagcctcga tcaacaagtg gtaccaatat ttcattggta gaattatctc tggtttaggt     540
gtcggtggta tcacagtttt atctcccatg ctaatatctg aggtcgcccc cagtgaaatg      600
agaggcacct ggtttcatg ttaccaagtc atgattactt taggtatttt cttaggttac       660
tgtaccaatt ttggtaccaa gaattactca aactctgtcc aatggagagt tccattaggt      720
ttgtgttttc gcctgggcctt atttatgatt ggtggtatga catttgttcc agagtctcca     780
cgttatttgg ctgaagtcgg taagatcgaa gaagccaaac gttctattgc cgtttataac     840
aaggttgctg ttgatgatcc atctgttttg gctgaagtcg aagctgtctt ggctggtgta      900
gaggcagaga aattagctgg taatgcatcc tggggtgaat tgtttagtag caagacaaag     960
```

| | |
|---|---|
| gtccttcagc gtttgatcat gggtgctatg attcaatctc tacaacaatt gacaggtgat | 1020 |
| aactatttct tctactatgg tactactatt ttcaaggctg ttggtttgag tgactctttc | 1080 |
| gaaacctcta ttgtcttggg tattgttaac tttgcttcca cctttgttgg tatttacgtt | 1140 |
| gttgagagat atggtcgtcg tacttgtttg ctatggggtg ctgcatccat gactgcttgt | 1200 |
| atggttgtct atgcttccgt gggtgtcacc agattatggc caaatggtca agaccaacca | 1260 |
| tcttccaagg gtgctggtaa ctgtatgatt gtctttgcct gtttctatat tttctgtttt | 1320 |
| gctactacat gggctccaat tccttatgtc gttgttctg aaactttccc attgagagtc | 1380 |
| aagtctaagg ctatgtctat tgctacagct gctaattggt gtggggtttt cttgattggt | 1440 |
| ttcttcactc catttattac tggtgctatt aacttctact acggttacgt tttcatgggc | 1500 |
| tgtttggtct tcatgttctt ctatgttttg ttagttgttc cagaaactaa gggttttgact | 1560 |
| ttggaagaag tcaacaccat gtgggaagaa ggtgttctac catggaagtc tgcctcatgg | 1620 |
| gttccaccat ccagaagagg tgccaactac gacgctgaag aaatgactca cgatgacaag | 1680 |
| ccattgtaca agagaatgtt cagcaccaaa taa | 1713 |

```
<210> SEQ ID NO 5
<211> LENGTH: 1693
<212> TYPE: DNA
<213> ORGANISM: Artificial Sequence
<220> FEATURE:
<223> OTHER INFORMATION: expression vector

<400> SEQUENCE: 5
```

| | |
|---|---|
| tctcgtagga acaatttcgg gccctgcgt gttcttctga ggttcatctt ttacatttgc | 60 |
| ttctgctgga taattttcag aggcaacaag gaaaaattag atggcaaaaa gtcgtctttc | 120 |
| aaggaaaaat ccccaccatc tttcgagatc cctgtaact tattggcaac tgaaagaatg | 180 |
| aaaaggagga aaatacaaaa tatactagaa ctgaaaaaaa aaagtataa atagagacga | 240 |
| tatatgccaa tacttcacaa tgttcgaatc tattcttcat ttgcagctat tgtaaaataa | 300 |
| taaaacatca agaacaaaca agctcaactt gtcttttcta agaacaaaga ataaacacaa | 360 |
| aaacaaaaag ttttttttaat tttaatcaaa aaatgtccac aaaatcatat accagtagag | 420 |
| ctgagactca tgcaagtccg gttgcatcga aacttttacg tttaatggat gaaaagaaga | 480 |
| ccaatttgtg tgcttctctt gacgttcgtt cgactgatga gctattgaaa cttgttgaaa | 540 |
| cgttgggtcc atacatttgc ctttttgaaaa cacacgttga tatcttggat gatttcagtt | 600 |
| atgagggtac tgtcgttcca ttgaaagcat tggcagagaa atacaagttc ttgatatttg | 660 |
| aggacagaaa attcgccgat atcggtaaca cagtcaaatt acaatataca tcgggcgttt | 720 |
| accgtatcgc agaatggtct gatatcacca acgcccacgg ggttactggt gctggtattg | 780 |
| ttgctggctt gaaacaaggt gcgcaagagg tcaccaaaga accaagggga ttattgatgc | 840 |
| ttgctgaatt gtcttccaag ggttctctag cacacggtga atatactaag ggtaccgttg | 900 |
| atattgcaaa gagtgataaa gatttcgtta ttgggttcat tgctcagaac gatatgggag | 960 |
| gaagagaaga agggttgat tggctaatca tgacccagg tgtaggttta gacgacaaag | 1020 |
| gcgatgcatt gggtcagcag tacagaaccg tcgacgaagt tgtaagtggt ggatcagata | 1080 |
| tcatcattgt tggcagagga cttttcgcca agggtagaga tcctaaggtt gaaggtgaaa | 1140 |
| gatacagaaa tgctggatgg gaagcgtacc aaaagagaat cagcgctccc cattaatttg | 1200 |
| cgaacacttt tattaattca tgatcacgct ctaaattgtg catttgaaat gtactctaat | 1260 |
| tctaatttta tattttaat gatatcttga aaagtaaata cgtttttaat atacaaaaa | 1320 |

```
taatacagtt taattttcaa gttttttgatc atttgttctc agaaagttga gtgggacgga    1380
gacaaagaaa ctttaaagag aaatgcaaag tgggaagaag tcagttgttt accgaccgca    1440
ctgttattca caaatattcc aattttgcct gcagacccac gtctacaaat tttggttagt    1500
ttggtaaatg gtaaggatat agtagagcct ttttgaaatg ggaaatatct tcttttctg     1560 tatcccgctt caaaagtgt ctaatgagtc agttatttct ttcttactca tcgcccgtca     1620
cttaaaagaa gaaaattac tttcatgatg cgaagcgaaa aaattttta gcttcaattt      1680 tcacaatgca tct                                                      1693

<210> SEQ ID NO 6
<211> LENGTH: 72
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 6
caaagaataa acacaaaaac aaaaagtttt tttaatttta atcaaaaaat gaattcaact     60
cccgatctaa ta                                                        72

<210> SEQ ID NO 7
<211> LENGTH: 36
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 7
ggagataaaa cggcaatacc accgacacct aaacca                              36

<210> SEQ ID NO 8
<211> LENGTH: 36
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 8
tggtttaggt gtcggtggta ttgccgtttt atctcc                              36

<210> SEQ ID NO 9
<211> LENGTH: 24
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 9
tttgtagacg tgggtctgca ggca                                           24

<210> SEQ ID NO 10
<211> LENGTH: 72
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 10
```

-continued caaagaataa acacaaaaac aaaaagttttt tttaattttta atcaaaaaat gaattcaact    60
cccgatctaa ta    72

<210> SEQ ID NO 11
<211> LENGTH: 41
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 11
ctggaacaaa tgtcatacca ccaatcataa ataaggccca g    41

<210> SEQ ID NO 12
<211> LENGTH: 41
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 12
ctgggcctta tttatgattg gtggtatgac atttgttcca g    41

<210> SEQ ID NO 13
<211> LENGTH: 24
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 13
tttgtagacg tgggtctgca ggca    24

<210> SEQ ID NO 14
<211> LENGTH: 34
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 14
ggactagtga tatctctcgt aggaacaatt tcgg    34

<210> SEQ ID NO 15
<211> LENGTH: 28
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 15
ggactagttg ctctgcaata gcagcgtc    28

<210> SEQ ID NO 16
<211> LENGTH: 70
<212> TYPE: DNA
<213> ORGANISM: Artificial Sequence
<220> FEATURE:
<223> OTHER INFORMATION: oligonucleotide primer with homolgy to S.
      cerevisiae sequences -continued

```
<400> SEQUENCE: 16
cctattcgtc atcgcagaca gccttcatct tctcgagata cacctggag cgcgcgtttc    60 ggtgatgacg                                                          70

<210> SEQ ID NO 17
<211> LENGTH: 73
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 17
aagtttcttt gtctccgtcc cactcaactt tctgagaaca aatgatccat tttttgatta    60
aaattaaaaa aac                                                      73

<210> SEQ ID NO 18
<211> LENGTH: 22
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 18
cctgcgtgtt cttctgaggt tc                                            22

<210> SEQ ID NO 19
<211> LENGTH: 24
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 19
tttgtagacg tgggtctgca ggca                                          24

<210> SEQ ID NO 20
<211> LENGTH: 74
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 20
caaagaataa acacaaaaac aaaagttttt tttaatttta atcaaaaaat gtccacaaaa    60
tcatatacca gtag                                                     74

<210> SEQ ID NO 21
<211> LENGTH: 72
<212> TYPE: DNA
<213> ORGANISM: Artificial Sequence
<220> FEATURE:
<223> OTHER INFORMATION: oligonucleotide primer with homolgy to S.
      cerevisiae sequences

<400> SEQUENCE: 21
gcacaaatta gagcgtgatc atgaattaat aaaagtgttc gcaaattaat ggggagcgct    60
gattctcttt tg                                                       72

<210> SEQ ID NO 22
```

<211> LENGTH: 570
<212> TYPE: PRT
<213> ORGANISM: Saccharomyces cerevisiae

<400> SEQUENCE: 22

```
Met Asn Ser Thr Pro Asp Leu Ile Ser Pro Gln Lys Ser Asn Ser Ser
1               5                   10                  15

Asn Ser Tyr Glu Leu Glu Ser Gly Arg Ser Lys Ala Met Asn Thr Pro
            20                  25                  30

Glu Gly Lys Asn Glu Ser Phe His Asp Asn Leu Ser Glu Ser Gln Val
        35                  40                  45

Gln Pro Ala Val Ala Pro Pro Asn Thr Gly Lys Gly Val Tyr Val Thr
    50                  55                  60

Val Ser Ile Cys Cys Val Met Val Ala Phe Gly Gly Phe Ile Phe Gly
65                  70                  75                  80

Trp Asp Thr Gly Thr Ile Ser Gly Phe Val Ala Gln Thr Asp Phe Leu
                85                  90                  95

Arg Arg Phe Gly Met Lys His His Asp Gly Ser His Tyr Leu Ser Lys
            100                 105                 110

Val Arg Thr Gly Leu Ile Val Ser Ile Phe Asn Ile Gly Cys Ala Ile
        115                 120                 125

Gly Gly Ile Val Leu Ala Lys Leu Gly Asp Met Tyr Gly Arg Arg Ile
    130                 135                 140

Gly Leu Ile Val Val Val Ile Tyr Thr Ile Gly Ile Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Thr Val Leu Ser Pro Met Leu Ile
            180                 185                 190

Ser Glu Val Ala Pro Ser Glu Met Arg Gly Thr Leu Val Ser Cys Tyr
        195                 200                 205

Gln Val Met Ile Thr Leu Gly Ile Phe Leu Gly Tyr Cys Thr Asn Phe
    210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Met Phe Val
                245                 250                 255

Pro Glu Ser Pro Arg Tyr Leu Val Glu Ala Gly Arg Ile Asp Glu Ala
            260                 265                 270

Arg Ala Ser Leu Ala Lys Val Asn Lys Cys Pro Pro Asp His Pro Tyr
        275                 280                 285

Ile Gln Tyr Glu Leu Glu Thr Ile Glu Ala Ser Val Glu Glu Met Arg
    290                 295                 300

Ala Ala Gly Thr Ala Ser Trp Gly Glu Leu Phe Thr Gly Lys Pro Ala
305                 310                 315                 320

Met Phe Gln Arg Thr Met Met Gly Ile Met Ile Gln Ser Leu Gln Gln
                325                 330                 335

Leu Thr Gly Asp Asn Tyr Phe Phe Tyr Tyr Gly Thr Ile Val Phe Gln
            340                 345                 350

Ala Val Gly Leu Ser Asp Ser Phe Glu Thr Ser Ile Val Phe Gly Val
        355                 360                 365

Val Asn Phe Phe Ser Thr Cys Cys Ser Leu Tyr Thr Val Asp Arg Phe
    370                 375                 380

Gly Arg Arg Asn Cys Leu Met Trp Gly Ala Val Gly Met Val Cys Cys
```

-continued

```
                385                 390                 395                 400

Tyr Val Val Tyr Ala Ser Val Gly Val Thr Arg Leu Trp Pro Asn Gly
                405                 410                 415

Gln Asp Gln Pro Ser Ser Lys Gly Ala Gly Asn Cys Met Ile Val Phe
            420                 425                 430

Ala Cys Phe Tyr Ile Phe Cys Phe Ala Thr Thr Trp Ala Pro Ile Ala
        435                 440                 445

Tyr Val Val Ile Ser Glu Cys Phe Pro Leu Arg Val Lys Ser Lys Cys
    450                 455                 460

Met Ser Ile Ala Ser Ala Ala Asn Trp Ile Trp Gly Phe Leu Ile Ser
465                 470                 475                 480

Phe Phe Thr Pro Phe Ile Thr Gly Ala Ile Asn Phe Tyr Tyr Gly Tyr
                485                 490                 495

Val Phe Met Gly Cys Met Val Phe Ala Tyr Phe Tyr Val Phe Phe Phe
                500                 505                 510

Val Pro Glu Thr Lys Gly Leu Ser Leu Glu Glu Val Asn Asp Met Tyr
            515                 520                 525

Ala Glu Gly Val Leu Pro Trp Lys Ser Ala Ser Trp Val Pro Val Ser
        530                 535                 540

Lys Arg Gly Ala Asp Tyr Asn Ala Asp Asp Leu Met His Asp Asp Gln
545                 550                 555                 560

Pro Phe Tyr Lys Ser Leu Phe Ser Arg Lys
                565                 570

<210> SEQ ID NO 23
<211> LENGTH: 541
<212> TYPE: PRT
<213> ORGANISM: Saccharomyces cerevisiae

<400> SEQUENCE: 23

Met Ser Glu Phe Ala Thr Ser Arg Val Glu Ser Gly Ser Gln Gln Thr
1               5                   10                  15

Ser Ile His Ser Thr Pro Ile Val Gln Lys Leu Glu Thr Asp Glu Ser
                20                  25                  30

Pro Ile Gln Thr Lys Ser Glu Tyr Thr Asn Ala Glu Leu Pro Ala Lys
            35                  40                  45

Pro Ile Ala Ala Tyr Trp Thr Val Ile Cys Leu Cys Leu Met Ile Ala
        50                  55                  60

Phe Gly Gly Phe Val Phe Gly Trp Asp Thr Gly Thr Ile Ser Gly Phe
65                  70                  75                  80

Val Asn Gln Thr Asp Phe Lys Arg Arg Phe Gly Gln Met Lys Ser Asp
                85                  90                  95

Gly Thr Tyr Tyr Leu Ser Asp Val Arg Thr Gly Leu Ile Val Gly Ile
            100                 105                 110

Phe Asn Ile Gly Cys Ala Phe Gly Gly Leu Thr Leu Gly Arg Leu Gly
        115                 120                 125

Asp Met Tyr Gly Arg Arg Ile Gly Leu Met Cys Val Val Leu Val Tyr
    130                 135                 140

Ile Val Gly Ile Val Ile Gln Ile Ala Ser Ser Asp Lys Trp Tyr Gln
145                 150                 155                 160

Tyr Phe Ile Gly Arg Ile Ile Ser Gly Met Gly Val Gly Gly Ile Ala
                165                 170                 175

Val Leu Ser Pro Thr Leu Ile Ser Glu Thr Ala Pro Lys His Ile Arg
            180                 185                 190
```

```
Gly Thr Cys Val Ser Phe Tyr Gln Leu Met Ile Thr Leu Gly Ile Phe
            195                 200                 205

Leu Gly Tyr Cys Thr Asn Tyr Gly Thr Lys Asp Tyr Ser Asn Ser Val
        210                 215                 220

Gln Trp Arg Val Pro Leu Gly Leu Asn Phe Ala Phe Ala Ile Phe Met
225                 230                 235                 240

Ile Ala Gly Met Leu Met Val Pro Glu Ser Pro Arg Phe Leu Val Glu
                245                 250                 255

Lys Gly Arg Tyr Glu Asp Ala Lys Arg Ser Leu Ala Lys Ser Asn Lys
            260                 265                 270

Val Thr Ile Glu Asp Pro Ser Ile Val Ala Glu Met Asp Thr Ile Met
        275                 280                 285

Ala Asn Val Glu Thr Glu Arg Leu Ala Gly Asn Ala Ser Trp Gly Glu
    290                 295                 300

Leu Phe Ser Asn Lys Gly Ala Ile Leu Pro Arg Val Ile Met Gly Ile
305                 310                 315                 320

Met Ile Gln Ser Leu Gln Gln Leu Thr Gly Asn Asn Tyr Phe Phe Tyr
                325                 330                 335

Tyr Gly Thr Thr Ile Phe Asn Ala Val Gly Met Lys Asp Ser Phe Gln
            340                 345                 350

Thr Ser Ile Val Leu Gly Ile Val Asn Phe Ala Ser Thr Phe Val Ala
        355                 360                 365

Leu Tyr Thr Val Asp Lys Phe Gly Arg Arg Lys Cys Leu Leu Gly Gly
    370                 375                 380

Ser Ala Ser Met Ala Ile Cys Phe Val Ile Phe Ser Thr Val Gly Val
385                 390                 395                 400

Thr Ser Leu Tyr Pro Asn Gly Lys Asp Gln Pro Ser Ser Lys Ala Ala
                405                 410                 415

Gly Asn Val Met Ile Val Phe Thr Cys Leu Phe Ile Phe Phe Phe Ala
            420                 425                 430

Ile Ser Trp Ala Pro Ile Ala Tyr Val Ile Val Ala Glu Ser Tyr Pro
        435                 440                 445

Leu Arg Val Lys Asn Arg Ala Met Ala Ile Ala Val Gly Ala Asn Trp
    450                 455                 460

Ile Trp Gly Phe Leu Ile Gly Phe Phe Thr Pro Phe Ile Thr Ser Ala
465                 470                 475                 480

Ile Gly Phe Ser Tyr Gly Tyr Val Phe Met Gly Cys Leu Val Phe Ser
                485                 490                 495

Phe Phe Tyr Val Phe Phe Phe Val Cys Glu Thr Lys Gly Leu Thr Leu
            500                 505                 510

Glu Glu Val Asn Glu Met Tyr Val Glu Gly Val Lys Pro Trp Lys Ser
        515                 520                 525

Gly Ser Trp Ile Ser Lys Glu Lys Arg Val Ser Glu Glu
    530                 535                 540

<210> SEQ ID NO 24
<211> LENGTH: 567
<212> TYPE: PRT
<213> ORGANISM: Saccharomyces cerevisiae

<400> SEQUENCE: 24

Met Asn Ser Thr Pro Asp Leu Ile Ser Pro Gln Lys Ser Ser Glu Asn
1               5                   10                  15

Ser Asn Ala Asp Leu Pro Ser Asn Ser Ser Gln Val Met Asn Met Pro
            20                  25                  30
```

-continued

```
Glu Glu Lys Gly Val Gln Asp Asp Phe Gln Ala Glu Ala Asp Gln Val
        35                  40                  45
Leu Thr Asn Pro Asn Thr Gly Lys Gly Ala Tyr Val Thr Val Ser Ile
     50                  55                  60
Cys Cys Val Met Val Ala Phe Gly Gly Phe Val Phe Gly Trp Asp Thr
 65                  70                  75                  80
Gly Thr Ile Ser Gly Phe Val Ala Gln Thr Asp Phe Leu Arg Arg Phe
                 85                  90                  95
Gly Met Lys His Lys Asp Gly Ser Tyr Tyr Leu Ser Lys Val Arg Thr
                100                 105                 110
Gly Leu Ile Val Ser Ile Phe Asn Ile Gly Cys Ala Ile Gly Gly Ile
            115                 120                 125
Ile Leu Ala Lys Leu Gly Asp Met Tyr Gly Arg Lys Met Gly Leu Ile
    130                 135                 140
Val Val Val Ile Tyr Ile Ile Gly Ile Ile Ile Gln Ile Ala Ser
145                 150                 155                 160
Ile Asn Lys Trp Tyr Gln Tyr Phe Ile Gly Arg Ile Ile Ser Gly Leu
                165                 170                 175
Gly Val Gly Gly Ile Ala Val Leu Ser Pro Met Leu Ile Ser Glu Val
            180                 185                 190
Ala Pro Lys Glu Met Arg Gly Thr Leu Val Ser Cys Tyr Gln Leu Met
        195                 200                 205
Ile Thr Leu Gly Ile Phe Leu Gly Tyr Cys Thr Asn Phe Gly Thr Lys
    210                 215                 220
Asn Tyr Ser Asn Ser Val Gln Trp Arg Val Pro Leu Gly Leu Cys Phe
225                 230                 235                 240
Ala Trp Ala Leu Phe Met Ile Gly Gly Met Thr Phe Val Pro Glu Ser
                245                 250                 255
Pro Arg Tyr Leu Val Glu Ala Gly Gln Ile Asp Glu Ala Arg Ala Ser
            260                 265                 270
Leu Ser Lys Val Asn Lys Val Ala Pro Asp His Pro Phe Ile Gln Gln
        275                 280                 285
Glu Leu Glu Val Ile Glu Ala Ser Val Glu Glu Ala Arg Ala Ala Gly
    290                 295                 300
Ser Ala Ser Trp Gly Glu Leu Phe Thr Gly Lys Pro Ala Met Phe Lys
305                 310                 315                 320
Arg Thr Met Met Gly Ile Met Ile Gln Ser Leu Gln Gln Leu Thr Gly
                325                 330                 335
Asp Asn Tyr Phe Phe Tyr Tyr Gly Thr Thr Val Phe Asn Ala Val Gly
            340                 345                 350
Met Ser Asp Ser Phe Glu Thr Ser Ile Val Phe Gly Val Val Asn Phe
        355                 360                 365
Phe Ser Thr Cys Cys Ser Leu Tyr Thr Val Asp Arg Phe Gly Arg Arg
    370                 375                 380
Asn Cys Leu Leu Tyr Gly Ala Ile Gly Met Val Cys Cys Tyr Val Val
385                 390                 395                 400
Tyr Ala Ser Val Gly Val Thr Arg Leu Trp Pro Asn Gly Glu Gly Asn
                405                 410                 415
Gly Ser Ser Lys Gly Ala Gly Asn Cys Met Ile Val Phe Ala Cys Phe
            420                 425                 430
Tyr Ile Phe Cys Phe Ala Thr Thr Trp Ala Pro Ile Ala Tyr Val Val
        435                 440                 445
```

```
Ile Ser Glu Thr Phe Pro Leu Arg Val Lys Ser Lys Ala Met Ser Ile
    450                 455                 460

Ala Thr Ala Ala Asn Trp Leu Trp Gly Phe Leu Ile Gly Phe Phe Thr
465                 470                 475                 480

Pro Phe Ile Thr Gly Ala Ile Asn Phe Tyr Tyr Gly Tyr Val Phe Met
                485                 490                 495

Gly Cys Met Val Phe Ala Tyr Phe Tyr Val Phe Phe Val Pro Glu
                500                 505                 510

Thr Lys Gly Leu Thr Leu Glu Glu Val Asn Asp Met Tyr Ala Glu Gly
            515                 520                 525

Val Leu Pro Trp Lys Ser Ala Ser Trp Val Pro Thr Ser Gln Arg Gly
    530                 535                 540

Ala Asn Tyr Asp Ala Asp Ala Leu Met His Asp Asp Gln Pro Phe Tyr
545                 550                 555                 560

Lys Lys Met Phe Gly Lys Lys
                565
```

<210> SEQ ID NO 25
<211> LENGTH: 576
<212> TYPE: PRT
<213> ORGANISM: Saccharomyces cerevisiae

<400> SEQUENCE: 25

```
Met Ser Glu Glu Ala Ala Tyr Gln Glu Asp Thr Ala Val Gln Asn Thr
1               5                   10                  15

Pro Ala Asp Ala Leu Ser Pro Val Glu Ser Asp Ser Asn Ser Ala Leu
            20                  25                  30

Ser Thr Pro Ser Asn Lys Ala Glu Arg Asp Asp Met Lys Asp Phe Asp
        35                  40                  45

Glu Asn His Glu Glu Ser Asn Asn Tyr Val Glu Ile Pro Lys Lys Pro
    50                  55                  60

Ala Ser Ala Tyr Val Thr Val Ser Ile Cys Cys Leu Met Val Ala Phe
65                  70                  75                  80

Gly Gly Phe Val Phe Gly Trp Asp Thr Gly Thr Ile Ser Gly Phe Val
                85                  90                  95

Ala Gln Thr Asp Phe Ile Arg Arg Phe Gly Met Lys His His Asp Gly
            100                 105                 110

Thr Tyr Tyr Leu Ser Lys Val Arg Thr Gly Leu Ile Val Ser Ile Phe
        115                 120                 125

Asn Ile Gly Cys Ala Ile Gly Gly Ile Ile Leu Ala Lys Leu Gly Asp
    130                 135                 140

Met Tyr Gly Arg Lys Met Gly Leu Ile Val Val Val Ile Tyr Ile
145                 150                 155                 160

Ile Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Ile Ala Val
            180                 185                 190

Leu Ser Pro Met Leu Ile Ser Glu Val Ser Pro Lys His Ile Arg Gly
        195                 200                 205

Thr Leu Val Ser Cys Tyr Gln Leu Met Ile Thr Leu Gly Ile Phe Leu
    210                 215                 220

Gly Tyr Cys Thr Asn Tyr Gly Thr Lys Thr Tyr Thr Asn Ser Val Gln
225                 230                 235                 240

Trp Arg Val Pro Leu Gly Leu Gly Phe Ala Trp Ala Leu Phe Met Ile
                245                 250                 255
```

Gly Gly Met Thr Phe Val Pro Glu Ser Pro Arg Tyr Leu Val Glu Val
                260                 265                 270

Gly Lys Ile Glu Glu Ala Lys Arg Ser Ile Ala Leu Ser Asn Lys Val
            275                 280                 285

Ser Ala Asp Asp Pro Ala Val Met Ala Glu Val Glu Val Val Gln Ala
        290                 295                 300

Thr Val Glu Ala Glu Lys Leu Ala Gly Asn Ala Ser Trp Gly Glu Ile
305                 310                 315                 320

Phe Ser Thr Lys Thr Lys Val Phe Gln Arg Leu Ile Met Gly Ala Met
                325                 330                 335

Ile Gln Ser Leu Gln Gln Leu Thr Gly Asp Asn Tyr Phe Phe Tyr Tyr
            340                 345                 350

Gly Thr Thr Val Phe Thr Ala Val Gly Leu Glu Asp Ser Phe Glu Thr
        355                 360                 365

Ser Ile Val Leu Gly Ile Val Asn Phe Ala Ser Thr Phe Val Gly Ile
    370                 375                 380

Phe Leu Val Glu Arg Tyr Gly Arg Arg Arg Cys Leu Leu Trp Gly Ala
385                 390                 395                 400

Ala Ser Met Thr Ala Cys Met Val Val Phe Ala Ser Val Gly Val Thr
                405                 410                 415

Arg Leu Trp Pro Asn Gly Lys Lys Asn Gly Ser Ser Lys Gly Ala Gly
            420                 425                 430

Asn Cys Met Ile Val Phe Thr Cys Phe Tyr Leu Phe Cys Phe Ala Thr
        435                 440                 445

Thr Trp Ala Pro Ile Pro Phe Val Val Asn Ser Glu Thr Phe Pro Leu
    450                 455                 460

Arg Val Lys Ser Lys Cys Met Ala Ile Ala Gln Ala Cys Asn Trp Ile
465                 470                 475                 480

Trp Gly Phe Leu Ile Gly Phe Phe Thr Pro Phe Ile Ser Gly Ala Ile
                485                 490                 495

Asp Phe Tyr Tyr Gly Tyr Val Phe Met Gly Cys Leu Val Phe Ser Tyr
            500                 505                 510

Phe Tyr Val Phe Phe Phe Val Pro Glu Thr Lys Gly Leu Thr Leu Glu
        515                 520                 525

Glu Val Asn Thr Leu Trp Glu Glu Gly Val Leu Pro Trp Lys Ser Pro
    530                 535                 540

Ser Trp Val Pro Pro Asn Lys Arg Gly Thr Asp Tyr Asn Ala Asp Asp
545                 550                 555                 560

Leu Met His Asp Asp Gln Pro Phe Tyr Lys Lys Met Phe Gly Lys Lys
                565                 570                 575

<210> SEQ ID NO 26
<211> LENGTH: 570
<212> TYPE: PRT
<213> ORGANISM: Saccharomyces cerevisiae

<400> SEQUENCE: 26

Met Ser Gln Asp Ala Ala Ile Ala Glu Gln Thr Pro Val Glu His Leu
1               5                   10                  15

Ser Ala Val Asp Ser Ala Ser His Ser Val Leu Ser Thr Pro Ser Asn
            20                  25                  30

Lys Ala Glu Arg Asp Glu Ile Lys Ala Tyr Gly Glu Gly Glu Glu His
        35                  40                  45

Glu Pro Val Val Glu Ile Pro Lys Arg Pro Ala Ser Ala Tyr Val Thr

```
              50                  55                  60
Val Ser Ile Met Cys Ile Met Ile Ala Phe Gly Gly Phe Val Phe Gly
 65                  70                  75                  80

Trp Asp Thr Gly Thr Ile Ser Gly Phe Ile Asn Gln Thr Asp Phe Ile
                 85                  90                  95

Arg Arg Phe Gly Met Lys His Lys Asp Gly Thr Asn Tyr Leu Ser Lys
                100                 105                 110

Val Arg Thr Gly Leu Ile Val Ser Ile Phe Asn Ile Gly Cys Ala Ile
                115                 120                 125

Gly Gly Ile Ile Leu Ser Lys Leu Gly Asp Met Tyr Gly Arg Lys Val
130                 135                 140

Gly Leu Ile Val Val Val Ile Tyr Ile Gly Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Ala Val Leu Ser Pro Met Leu Ile
                180                 185                 190

Ser Glu Val Ser Pro Lys His Leu Arg Gly Thr Leu Val Ser Cys Tyr
                195                 200                 205

Gln Leu Met Ile Thr Ala Gly Ile Phe Leu Gly Tyr Cys Thr Asn Phe
                210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
                260                 265                 270

Lys Arg Ser Ile Ala Val Ser Asn Lys Val Ala Val Asp Asp Pro Ser
                275                 280                 285

Val Leu Ala Glu Val Glu Ala Val Leu Ala Gly Val Glu Ala Glu Lys
                290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
                325                 330                 335

Leu Thr Gly Asp Asn Tyr Phe Phe Tyr Tyr Gly Thr Thr Ile Phe Lys
                340                 345                 350

Ala Val Gly Leu Ser Asp Ser Phe Glu Thr Ser Ile Val Leu Gly Ile
                355                 360                 365

Val Asn Phe Ala Ser Thr Phe Val Gly Ile Tyr Val Val Glu Arg Tyr
                370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
                405                 410                 415

Gln Asp Gln Pro Ser Ser Lys Gly Ala Gly Asn Cys Met Ile Val Phe
                420                 425                 430

Ala Cys Phe Tyr Ile Phe Cys Phe Ala Thr Thr Trp Ala Pro Ile Pro
                435                 440                 445

Tyr Val Val Val Ser Glu Thr Phe Pro Leu Arg Val Lys Ser Lys Ala
                450                 455                 460

Met Ser Ile Ala Thr Ala Ala Asn Trp Leu Trp Gly Phe Leu Ile Gly
465                 470                 475                 480
```

-continued

Phe Phe Thr Pro Phe Ile Thr Gly Ala Ile Asn Phe Tyr Tyr Gly Tyr
                485                 490                 495

Val Phe Met Gly Cys Leu Val Phe Met Phe Phe Tyr Val Leu Leu Val
            500                 505                 510

Val Pro Glu Thr Lys Gly Leu Thr Leu Glu Glu Val Asn Thr Met Trp
        515                 520                 525

Glu Glu Gly Val Leu Pro Trp Lys Ser Ala Ser Trp Val Pro Pro Ser
    530                 535                 540

Arg Arg Gly Ala Asn Tyr Asp Ala Glu Glu Met Ala His Asp Asp Lys
545                 550                 555                 560

Pro Leu Tyr Lys Arg Met Phe Ser Thr Lys
                565                 570

<210> SEQ ID NO 27
<211> LENGTH: 570
<212> TYPE: PRT
<213> ORGANISM: Saccharomyces cerevisiae

<400> SEQUENCE: 27

Met Ser Gln Asp Ala Ala Ile Ala Glu Gln Thr Pro Val Glu His Leu
1               5                   10                  15

Ser Ala Val Asp Ser Ala Ser His Ser Val Leu Ser Thr Pro Ser Asn
            20                  25                  30

Lys Ala Glu Arg Asp Glu Ile Lys Ala Tyr Gly Glu Gly Glu Glu His
        35                  40                  45

Glu Pro Val Val Glu Ile Pro Lys Arg Pro Ala Ser Ala Tyr Val Thr
    50                  55                  60

Val Ser Ile Met Cys Ile Met Ile Ala Phe Gly Gly Phe Val Phe Gly
65                  70                  75                  80

Trp Asp Thr Gly Thr Ile Ser Gly Phe Ile Asn Gln Thr Asp Phe Ile
                85                  90                  95

Arg Arg Phe Gly Met Lys His Lys Asp Gly Thr Asn Tyr Leu Ser Lys
            100                 105                 110

Val Arg Thr Gly Leu Ile Val Ser Ile Phe Asn Ile Gly Cys Ala Ile
        115                 120                 125

Gly Gly Ile Ile Leu Ser Lys Leu Gly Asp Met Tyr Gly Arg Lys Val
    130                 135                 140

Gly Leu Ile Val Val Val Ile Tyr Ile Ile Gly Ile Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Ala Val Leu Ser Pro Met Leu Ile
            180                 185                 190

Ser Glu Val Ser Pro Lys His Leu Arg Gly Thr Leu Val Ser Cys Tyr
        195                 200                 205

Gln Leu Met Ile Thr Ala Gly Ile Phe Leu Gly Tyr Cys Thr Asn Phe
    210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
            260                 265                 270

Lys Arg Ser Ile Ala Val Ser Asn Lys Val Ala Val Asp Asp Pro Ser

-continued

|     | 275 |     |     | 280 |     |     | 285 |     |     |     |     |
|-----|-----|-----|-----|-----|-----|-----|-----|-----|-----|-----|-----|
Val Leu Ala Glu Val Glu Ala Val Leu Ala Gly Val Glu Ala Glu Lys
            290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
            325                 330                 335

Leu Thr Gly Asp Asn Tyr Phe Phe Tyr Tyr Gly Thr Thr Ile Phe Lys
            340                 345                 350

Ala Val Gly Leu Ser Asp Ser Phe Glu Thr Ser Ile Val Leu Gly Ile
            355                 360                 365

Val Asn Phe Ala Ser Thr Phe Val Gly Ile Tyr Val Val Glu Arg Tyr
            370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
            405                 410                 415

Gln Asp Gln Pro Ser Ser Lys Gly Ala Gly Asn Cys Met Ile Val Phe
            420                 425                 430

Ala Cys Phe Tyr Ile Phe Cys Phe Ala Thr Thr Trp Ala Pro Ile Pro
            435                 440                 445

Tyr Val Val Val Ser Glu Thr Phe Pro Leu Arg Val Lys Ser Lys Ala
            450                 455                 460

Met Ser Ile Ala Thr Ala Ala Asn Trp Leu Trp Gly Phe Leu Ile Gly
465                 470                 475                 480

Phe Phe Thr Pro Phe Ile Thr Gly Ala Ile Asn Phe Tyr Tyr Gly Tyr
            485                 490                 495

Val Phe Met Gly Cys Leu Val Phe Met Phe Phe Tyr Val Leu Leu Val
            500                 505                 510

Val Pro Glu Thr Lys Gly Leu Thr Leu Glu Glu Val Asn Thr Met Trp
            515                 520                 525

Glu Glu Gly Val Leu Pro Trp Lys Ser Ala Ser Trp Val Pro Pro Ser
            530                 535                 540

Arg Arg Gly Ala Asn Tyr Asp Ala Glu Glu Met Thr His Asp Asp Lys
545                 550                 555                 560

Pro Leu Tyr Lys Arg Met Phe Ser Thr Lys
            565                 570

<210> SEQ ID NO 28
<211> LENGTH: 574
<212> TYPE: PRT
<213> ORGANISM: Saccharomyces cerevisiae

<400> SEQUENCE: 28

Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Ser Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

-continued

```
Gly Gly Phe Met Phe Gly Trp Asp Thr Gly Thr Ile Ser Gly Phe Val
                 85                  90                  95

Val Gln Thr Asp Phe Leu Arg Arg Phe Gly Met Lys His Lys Asp Gly
                100                 105                 110

Thr His Tyr Leu Ser Asn Val Arg Thr Gly Leu Ile Val Ala Ile Phe
                115                 120                 125

Asn Ile Gly Cys Ala Phe Gly Gly Ile Ile Leu Ser Lys Gly Gly Asp
            130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
                180                 185                 190

Leu Cys Pro Met Leu Ile Ser Glu Ile Ala Pro Lys His Leu Arg Gly
                195                 200                 205

Thr Leu Val Ser Cys Tyr Gln Leu Met Ile Thr Ala Gly Ile Phe Leu
            210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
                260                 265                 270

Asn Lys Val Glu Asp Ala Lys Arg Ser Ile Ala Lys Ser Asn Lys Val
            275                 280                 285

Ser Pro Glu Asp Pro Ala Val Gln Ala Glu Leu Asp Leu Ile Met Ala
290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
                340                 345                 350

Gly Thr Val Ile Phe Lys Ser Val Gly Leu Asp Asp Ser Phe Glu Thr
            355                 360                 365

Ser Ile Val Ile Gly Val Val Asn Phe Ala Ser Thr Phe Phe Ser Leu
370                 375                 380

Trp Thr Val Glu Asn Leu Gly His Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
                420                 425                 430

Asn Cys Met Ile Val Phe Thr Cys Phe Tyr Ile Phe Cys Tyr Ala Thr
            435                 440                 445

Thr Trp Ala Pro Val Ala Trp Val Ile Thr Ala Glu Ser Phe Pro Leu
            450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
```

-continued

```
              500               505              510
Phe Tyr Val Phe Phe Phe Val Pro Glu Thr Lys Gly Leu Ser Leu Glu
        515              520              525

Glu Ile Gln Glu Leu Trp Glu Glu Gly Val Leu Pro Trp Lys Ser Glu
        530              535              540

Gly Trp Ile Pro Ser Ser Arg Arg Gly Asn Asn Tyr Asp Leu Glu Asp
545              550              555              560

Leu Gln His Asp Asp Lys Pro Trp Tyr Lys Ala Met Leu Glu
                565              570
```